United States Patent
Bremer et al.

(10) Patent No.: US 7,087,272 B2
(45) Date of Patent: Aug. 8, 2006

(54) FLUORINATED FLUORENE DERIVATIVES

(75) Inventors: Matthias Bremer, Darmstadt (DE);
Detlef Pauluth, Ober-Ramstadt (DE);
Melanie Klasen-Memmer,
Heuchelheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/473,332

(22) PCT Filed: Mar. 7, 2002

(86) PCT No.: PCT/EP02/02503

§ 371 (c)(1),
(2), (4) Date: Sep. 29, 2003

(87) PCT Pub. No.: WO02/079344

PCT Pub. Date: Oct. 10, 2002

(65) Prior Publication Data

US 2004/0106798 A1    Jun. 3, 2004

(30) Foreign Application Priority Data

Mar. 30, 2001  (DE) ................. 101 15 955

(51) Int. Cl.
C09K 19/32   (2006.01)
C07C 25/00   (2006.01)
C07C 23/08   (2006.01)
C07C 23/18   (2006.01)

(52) U.S. Cl. ............. 428/1.1; 252/299.01; 252/299.62; 570/127; 570/129; 570/183; 570/187

(58) Field of Classification Search ................ 549/458; 428/1.1; 252/299.61, 299.63, 299.67, 299.01, 252/299.62; 570/127, 129, 183, 187
See application file for complete search history.

(56) References Cited

U.S. PATENT DOCUMENTS

| | | | |
|---|---|---|---|
| 6,677,479 B1 * | 1/2004 | Schmidt et al. | 562/474 |
| 6,793,984 B1 * | 9/2004 | Bremer et al. | 428/1.1 |
| 2004/0124399 A1 * | 7/2004 | Schmidt et al. | 252/299.62 |

FOREIGN PATENT DOCUMENTS

| | | | |
|---|---|---|---|
| DE | 197 20 289 A | | 11/1998 |
| DE | 10101022 | * | 7/2002 |
| EP | 1201632 | * | 5/2002 |
| EP | 1223209 | * | 7/2002 |
| EP | 1223210 | * | 7/2002 |
| JP | 20001 048823 A | | 2/2001 |
| JP | 2001 064216 A | | 3/2001 |
| WO | WO 01 10803 A | | 2/2001 |

OTHER PUBLICATIONS

CAPLUS 1961: 144020.*
CAPLUS 1972: 525665.*
CAPLUS 1989: 515735.*
Barton, T.J.; Witiak, J.L.; McIntosh, C.L.: "Thermal decomposition of 1, 4-diphenyl-2, 3-bis-(trifluoromethyl)-7-d imethylsilabicyclo'2.2.1! heptadiene" J. Am. Chem. Soc. Bd 94, Nr. 17, 1972, Seiten 6229-6230.
Carpino, L.A.; Chao, H.G.; Tien, J.-H.: "Investigation of the reaction between amino acids or amino acid esters and -9formylfluorene and its equivalents. Possible utility of the derived enamies as amino group protectants." J. Org. Chem., Bd. 54, Nr. 18, 1989, Seiten 4302-4313.
Suzuki, K.; Weisburger, E.K.; Weisburger J.H.: "Nitration of 1- and 3-fluorofluorene" J. Org. Chem, Bd. 24 Oct. 1959 Seiten 1511-1517.

* cited by examiner

*Primary Examiner*—Shean C Wu
(74) *Attorney, Agent, or Firm*—Millen, White, Zelano, Branigan, P.C.

(57) ABSTRACT

The invention relates to fluorinated fluorene derivatives of negative DC anisotropy, of the formula I

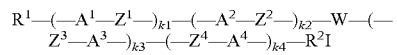

in which
W denotes the sub-formula

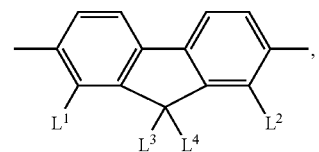

$L^1$ and $L^2$, independently of one another, are H, F, Cl, —$CH_2F$, —$CHF_2$ or —$CF_3$, with the proviso that $L^1$ and $L^2$ are not both H,
$L^3$ and $L^4$, independently of one another, are H or F, and $R^1$, $R^2$, $A^1$, $A^2$, $A^3$, $A^4$, $Z^1$, $Z^2$, $Z^3$, $Z^4$, k1, k2, k3 and k4 are as defined above. The invention furthermore relates to liquid-crystalline media and to optical and electro-optical display elements.

8 Claims, No Drawings

FLUORINATED FLUORENE DERIVATIVES

The invention relates to fluorinated fluorene derivatives of the formula I which have negative anisotropy of the dielectric constants (DC anisotropy),

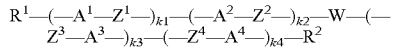

$$R^1-(-A^1-Z^1-)_{k1}-(-A^2-Z^2-)_{k2}-W-(-Z^3-A^3-)_{k3}-(-Z^4-A^4-)_{k4}-R^2 \quad I$$

in which
W is the

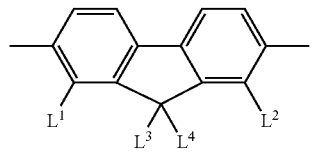

group, $L^1$ and $L^2$, independently of one another, are H, F, Cl, $-CH_2F$, $-CHF_2$ or $-CF_3$, with the proviso that $L^1$ and $L^2$ are not both H, $L^3$ and $L^4$, independently of one another, are H or F, $R^1$ and $R^2$, independently of one another, are H, halogen, —CN, —NCS, —SF$_5$ or alkyl having from 1 to 18 carbon atoms, in which, in addition, one or two non-adjacent —CH$_2$— groups may be replaced by —O—, —S—, —CO—, —O—CO—, —CO—O—, —E— and/or —C≡C— and/or in which, in addition, one or more H atoms may be replaced by halogen and/or —CN, E is $CR^4{=}CR^5$ or $CHR^4{-}CHR^5$, $R^4$ and $R^5$ are each, independently of one another, H, alkyl having 1–6 carbon atoms, F, Cl, CF$_3$ or CN, $A^1, A^2, A^3$ and $A^4$ are each, independently of one another, 1,4-phenylene, in which one or more CH groups may be replaced by N, 1,4-cyclohexylene, in which one or two non-adjacent CH$_2$ groups may be replaced by O and/or S, 1,4-cyclohexenylene, 1,4-bicyclo[2.2.2]octylene, piperidine-1,4-diyl, naphthalene-2,6-diyl, decahydronaphthalene-2,6-diyl or 1,2,3,4-tetrahydronaphthalene-2,6-diyl, where, in the meanings given for $A^1, A^2, A^3$ and $A^4$, one or more H atoms may be substituted by halogen, —CN and/or alkyl having from 1 to 6 carbon atoms, in which one or more H atoms may be replaced by halogen or —CN, and/or in which one or more non-adjacent —CH$_2$— groups may be replaced, independently of one another, by —CO—, —O—CO—, —CO—O—, —O—, —S—, —CH=CH— or —C≡C—, and $Z^1, Z^2, Z^3$ and $Z^4$, independently of one another, are —O—CO—, —CO—O—, —CH$_2$—O—, —CF$_2$—O—, —O—CH$_2$—, —O—CF$_2$—, —C$_2$H$_4$—, —CH$_2$—CF$_2$—, —CF$_2$—CH$_2$—, —CF$_2$—CF$_2$—, —CH=CH—, —CF=CH—, —CH=CF—, —CF=CF—, —C≡C— or a single bond, k1, k2, k3 and k4, independently of one another, are 0, 1 or 2.

The invention furthermore relates to liquid-crystalline media which comprise the liquid-crystalline media according to the invention and to liquid-crystal and electro-optical display elements which contain the liquid-crystalline media according to the invention.

Fluorinated fluorene derivatives which contain the

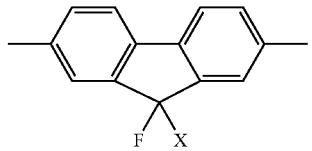

group in which X is F or H are described in DE 197 20 289 as components of ferroelectric liquid-crystal mixtures. It is stated in this respect that more negative values of the dielectric anisotropy (Δε) can be obtained by admixing compounds of this type. Use in FLC mixtures for operation in inverse mode is cited as preferred. However, values for individual substances or mixtures are not given.

There continues to be a great demand for compounds and media having highly to very highly negative dielectric anisotropy Δε, in particular for those having very high specific resistance at the same time as a broad mesophase range and low viscosity.

The object of the present-invention is to provide novel, stable, liquid-crystalline or mesogenic compounds having highly to very highly negative DC anisotropy which are suitable as components of liquid-crystalline media.

The invention furthermore relates to the provision of liquid-crystalline media and optical and electro-optical display elements.

The first-mentioned object is achieved by means of fluorene derivatives of the formula I. It has been found that the compounds according to the invention are eminently suitable as components of liquid-crystalline media. They can be used to obtain stable liquid-crystalline media which are particularly suitable for electro-optical LC displays. The fluorene derivatives according to the invention have highly to very highly negative Δε values. In general, these values are significantly lower than the Δε values of comparable compounds which carry exclusively H atoms in the 1- and 8-position of the fluorene group. In addition, the fluorene derivatives according to the invention have relatively low values of the optical anisotropy Δn and mesophase ranges which are favourable for use in electro-optical display elements. Furthermore, these compounds are also stable chemically, thermally and to the action of light and are readily miscible with other liquid-crystalline substances.

The provision of the fluorene derivatives according to the invention very generally considerably broadens the range of liquid-crystalline substances which are suitable, from various applicational points of view, for the preparation of liquid-crystalline mixtures.

In addition, the invention relates to a liquid-crystalline medium having two or more liquid-crystalline components, where the medium has at least one fluorene derivative according to the invention. The use of fluorene derivatives according to the invention enables the dielectric anisotropy of media of this type to be influenced in a targeted manner towards negative Δε values, with low viscosities advantageously being achieved. In addition, however, it is also possible to add one or more compounds according to the invention to liquid-crystalline media in order to modify the optical anisotropy and/or the mesophase ranges and/or the tilt angle of media of this type in a targeted manner.

The compounds according to the invention can be used as components of liquid-crystalline media, in particular for displays based on the principle of the twisted cell, the guest-host effect, the DAP (deformation of aligned phases), ECB (electrically controlled birefringence), CSH (colour super homeotropic), VA (vertically aligned) or IPS (in-plane switching) effect or the effect of dynamic scattering.

Furthermore, the compounds according to the invention can be used as components of optically active, tilted, smectic (ferroelectric) liquid-crystalline media, in particular for displays based on the SSFLCD (surface stabilised ferroelectric liquid crystal display) effect of Clark and Lagerwall, but also on the DHF (distorted helix formation) effect or the PSFLCD (pitch stabilised ferroelectric liquid crystal display) effect, which is also known as the SBF (short pitch bistable ferroelectric) effect.

The invention furthermore relates to an optical display element which contains a liquid-crystalline medium according to the invention, and to an electro-optical display element which contains a liquid-crystalline medium according to the invention as dielectric. The above-mentioned display elements are preferred here.

Above and below, the groups, substituents and indices W, $R^1$, $R^2$, E, $R^4$, $R^5$, $L^1$, $L^2$, $L^3$, $L^4$, $Z^1$, $Z^2$, $Z^3$, $Z^4$, $A^1$, $A^2$, $A^3$, $A^4$, k1, k2, k3 and k4 are as defined in respect of the formula I, unless expressly stated otherwise. If a radical occurs more than once, it may adopt identical or different meanings.

The meaning of the formula I includes all isotopes of the chemical elements bonded in the compounds of the formula I. In enantiomerically pure or enriched form, the compounds of the formula I are also suitable as chiral dopants and in general for achieving chiral mesophases.

Preferred meanings of groups and substituents of the fluorene derivatives according to the invention are indicated below.

Preferred meanings of the group W are represented by the sub-formulae W1 to W3:

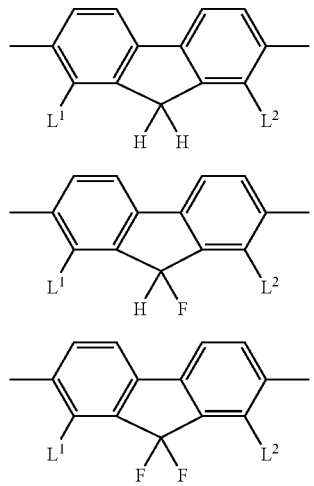

Particularly preferred meanings of the sub-formula W1 are represented by the sub-formulae W11 to W18:

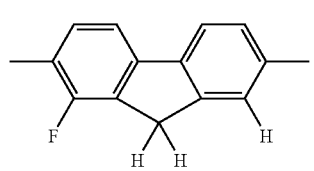

Above and below, I=0, 1 or 2, and consequently the —$CH_IF_{3-I}$ group is —$CH_2F$, —$CHF_2$ or —$CF_3$. I preferably has the value 0 or 1, particularly preferably the value I=0. If the index I occurs more than once in a formula, this may have identical or different meanings.

Particularly preferred meanings of the sub-formula W2 are represented by the sub-formulae W21 to W28:

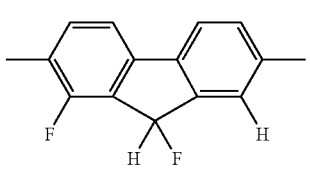

-continued

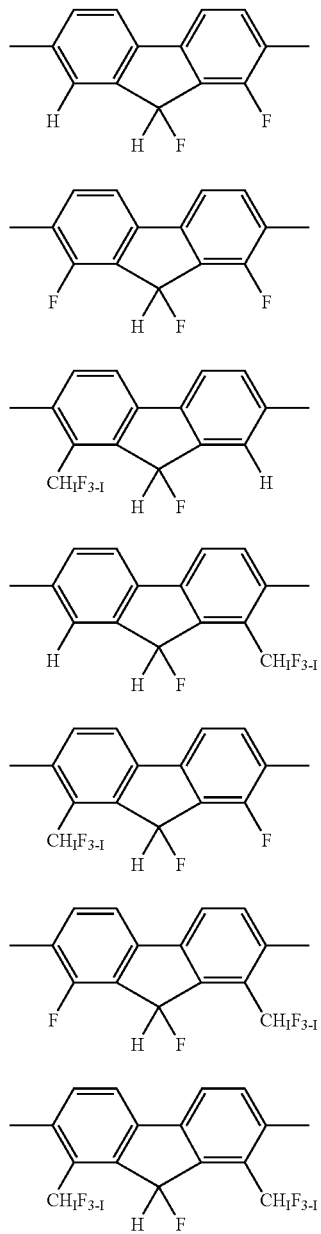

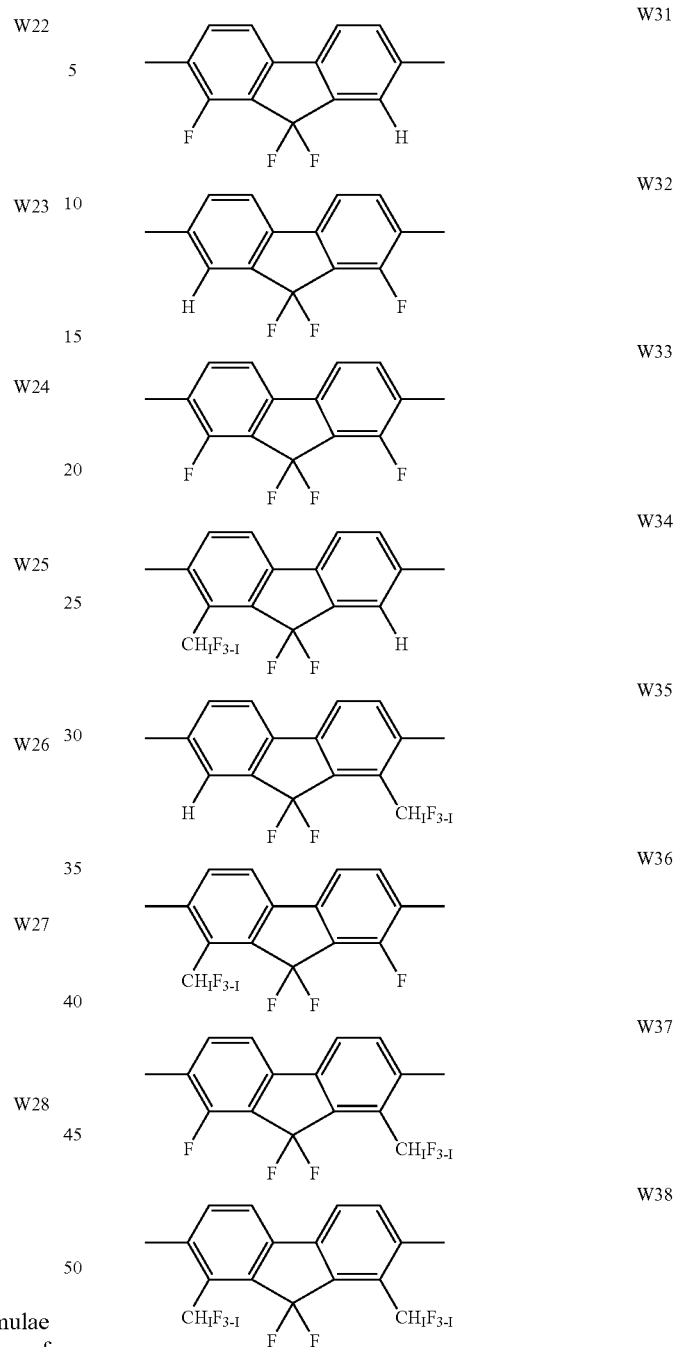

The sub-formula W2 and the corresponding sub-formulae W21 to W28 include, in the case where the carbon atom of the

group is a chiral centre, both the racemates and the enantiomerically pure or enriched forms.

Particularly preferred meanings of the sub-formula W3 are represented by the sub-formulae W31 to W38:

Of the above-mentioned sub-formulae, W1, in particular W11 to W18, and W3, in particular W31 to W38, are very particularly preferred.

According to a first preferred embodiment of the invention, k1, k2, k3 and k4 have the value 0, and the compounds according to the invention therefore have the formula Ia $$R^1—W—R^2 \quad \text{Ia.}$$

At least one of the groups $R^1$ or $R^2$ here, preferably $R^1$ and $R^2$, has, independently of one another, the meaning alkyl having from 1 to 18 carbon atoms, in which, in addition, one or two non-adjacent —CH$_2$— groups and/or in addition one or more H atoms may be replaced as indicated.

Particular preference is given to compounds of the sub-formulae Ia1 to Ia10

| | |
|---|---|
| R$^1$-W11-R$^2$ | Ia1 |
| R$^1$-W13-R$^2$ | Ia2 |
| R$^1$-W14-R$^2$ | Ia3 |
| R$^1$-W16-R$^2$ | Ia4 |
| R$^1$-W18-R$^2$ | Ia5 |
| R$^1$-W31-R$^2$ | Ia6 |
| R$^1$-W33-R$^2$ | Ia7 |
| R$^1$-W34-R$^2$ | Ia8 |
| R$^1$-W36-R$^2$ | Ia9 |
| R$^1$-W38-R$^2$ | Ia10 | with the meanings indicated above for W11 to W38.

According to a second preferred embodiment, at least one of the indices k1, k2, k3 and/or k4 has a value not equal to zero.

According to a preferred first variant in this respect, k1=1 and k2=k3=k4=0, so that the fluorene derivatives have the formula Ib $$R^1—A^1—Z^1—W—R^2 \qquad Ib.$$

According to a preferred second variant, k1=k2=1 and k3=k4=0, so that the fluorene derivatives have the formula Ic $$R^1—A^1—Z^1—A^2—Z^2—W—R^2 \qquad Ic.$$

According to a preferred third variant, k1=k3=1 and k2=k4=0, so that the fluorene derivatives have the formula Id $$R^1—A^1—Z^1—W—Z^3—A^3—R^2 \qquad Id.$$

Particularly preferred meanings of A$^1$, A$^2$, A$^3$ and/or A$^4$ are, independently of one another, 1,4-phenylene, which may be monosubstituted, disubstituted or trisubstituted by fluorine, trans-1,4-cyclohexylene and 1,3-dioxane-2,5-diyl, for which, for reasons of simplicity, the abbreviations Phe, Cyc and Dio respectively are used below.

The term 1,3-dioxane-2,5-diyl in each case covers the two positional isomers

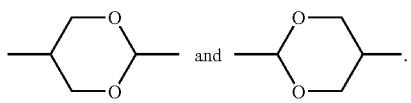

If, in accordance with the second embodiment, the compounds contain a six-membered ring in addition to the group W, the following compounds of the sub-formulae Ib1 to Ib3 are preferred:

| | |
|---|---|
| R$^1$-Cyc-Z$^1$—W—R$^2$ | Ib1 |
| R$^1$-Phe-Z$^1$—W—R$^2$ | Ib2 |
| R$^1$-Dio-Z$^1$—W—R$^2$ | Ib3 |

If, in accordance with the second embodiment, the compounds contain two six-membered rings in addition to the group W, the following compounds of the sub-formulae Ic1 to Ic9 and Id1 to Id9 are preferred:

| | |
|---|---|
| R$^1$-Cyc-Z$^1$-Cyc-Z$^2$—W—R$^2$ | Ic1 |
| R$^1$-Cyc-Z$^1$-Phe-Z$^2$—W—R$^2$ | Ic2 |
| R$^1$-Cyc-Z$^1$-Dio-Z$^2$—W—R$^2$ | Ic3 |
| R$^1$-Phe-Z$^1$-Cyc-Z$^2$—W—R$^2$ | Ic4 |
| R$^1$-Phe-Z$^1$-Phe-Z$^2$—W—R$^2$ | Ic5 |
| R$^1$-Phe-Z$^1$-Dio-Z$^2$—W—R$^2$ | Ic6 |
| R$^1$-Dio-Z$^1$-Cyc-Z$^2$—W—R$^2$ | Ic7 |
| R$^1$-Dio-Z$^1$-Phe-Z$^2$—W—R$^2$ | Ic8 |
| R$^1$-Dio-Z$^1$-Dio-Z$^2$—W—R$^2$ | Ic9 |
| R$^1$-Cyc-Z$^1$—W—Z$^3$-Cyc-R$^2$ | Id1 |
| R$^1$-Cyc-Z$^1$—W—Z$^3$-Phe-R$^2$ | Id2 |
| R$^1$-Cyc-Z$^1$—W—Z$^3$-Dio-R$^2$ | Id3 |
| R$^1$-Phe-Z$^1$—W—Z$^3$-Cyc-R$^2$ | Id4 |
| R$^1$-Phe-Z$^1$—W—Z$^3$-Phe-R$^2$ | Id5 |
| R$^1$-Phe-Z$^1$—W—Z$^3$-Dio-R$^2$ | Id6 |
| R$^1$-Dio-Z$^1$—W—Z$^3$-Cyc-R$^2$ | Id7 |
| R$^1$-Dio-Z$^1$—W—Z$^3$-Phe-R$^2$ | Id8 |
| R$^1$-Dio-Z$^1$—W—Z$^3$-Dio-R$^2$ | Id9 |

The compounds in accordance with the second embodiment may also contain three or more six-membered rings in addition to the group W.

If L$^3$ and L$^4$ are H, preference is given to the fluorene derivatives of the formula I in which R$^1$—(—A$^1$—Z$^1$—)$_{k1}$—(—A$^2$—Z$^2$—)$_{k2}$— and —(—Z$^3$—A$^3$—)$_{k3}$—(—Z$^4$—A$^4$—)$_{k4}$—R$^2$ are selected in such a way that the fluorene derivative has a dielectric anisotropy Δε of less than or equal to −2.0, particularly preferably less than or equal to −4.0, very particularly preferably less than or equal to −5.0.

If L$^3$ or L$^4$ is F and the other substituent L$^4$ or L$^3$ is H, preference is given to the fluorene derivatives of the formula I in which R$^1$—(—A$^1$—Z$^1$—)$_{k1}$—(—A$^2$—Z$^2$—)$_{k2}$— and —(—Z$^3$—A$^3$—)$_{k3}$—(—Z$^4$—A$^4$—)$_{k4}$—R$^2$ are selected in such a way that the fluorene derivative has a dielectric anisotropy Δε of less than or equal to −6.0, particularly preferably less than or equal to −8.0, very particularly preferably less than or equal to −10.0.

If L$^3$ and L$^4$ are F, preference is given to the fluorene derivatives of the formula I in which R$^1$—(—A$^1$—Z$^1$—)$_{k1}$—(—A$^2$—Z$^2$—)$_{k2}$— and —(—Z$^3$—A$^3$—)$_{k3}$—(—Z$^4$—A$^4$—)$_{k4}$—R$^2$ are selected in such a way that the fluorene derivative has a dielectric anisotropy Δε of less than or equal to −8.0, in particular less than or equal to −10.0, particularly preferably less than or equal to −12.0, very particularly preferably less than or equal to −15.0.

In the case of the meaning alkyl in the groups or substituents indicated above or below, in particular in R$^1$ and/or R$^2$, the alkyl radical may be linear or branched. It preferably has 1, 2, 3, 4, 5, 6, 7 or 8 carbon atoms. It is preferably linear and is therefore particularly methyl, ethyl, propyl, butyl, pentyl, hexyl, heptyl or octyl.

$R^1$ and/or $R^2$ are preferably alkyl, alkenyl, alkoxy, alkenyloxy, oxaalkyl, oxaalkenyl, alkylcarbonyloxy or alkyloxycarbonyl.

Besides the above-mentioned meanings in the case of alkyl, $R^1$ and $R^2$ as alkyl may also have more than 8 carbon atoms and are therefore particularly nonyl, decyl, undecyl, dodecyl, tridecyl, tetradecyl or pentadecyl.

Further preferred meanings of $R^1$ and/or $R^2$ are alkoxy. The alkoxy radical may be linear or branched. It is preferably linear and has 1, 2, 3, 4, 5, 6, 7 or 8 carbon atoms and is therefore particularly methoxy, ethoxy, propoxy, butoxy, pentoxy, hexoxy, heptoxy or octoxy, furthermore nonoxy, decoxy, undecoxy, dodecoxy, tridecoxy or tetradecoxy.

Furthermore, $R^1$ and/or $R^2$ are preferably oxaalkyl. The radical may be linear or branched. It is preferably linear and is, for example, 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7- 8- or 9-oxadecyl.

If $R^1$ and/or $R^2$ are an alkenyl radical, this may be straight-chain or branched. It is preferably straight-chain and has from 2 to 8 carbon atoms. Accordingly, it is in particular vinyl, prop-1- or -2-enyl, but-1-, -2- or -3-enyl, pent-1-, -2-, -3- or 4-enyl, hex-1-, -2-, -3-, -4- or -5-enyl, hept-1-, -2-, -3-, -4-, -5- or -6-enyl or oct-1-, -2-, -3-, -4-, -5-, -6- or -7-enyl.

If $R^1$ and/or $R^2$ is an alkenyloxy radical, this may be straight-chain or branched. It is preferably straight-chain and accordingly is in particular vinyloxy, prop-1- or -2-enyloxy, but-1-, -2- or -3-enyloxy, pent-1-, -2-, -3- or -4-enyloxy, hex-1-, -2-, -3-, -4- or -5-enyloxy, hept-1-, -2-, -3-, -4-, -5- or -6-enyloxy or oct-1-, -2-, -3-, -4-, -5-, -6- or -7-enyloxy.

If $R^1$ and/or $R^2$ are an oxaalkenyl radical, this may be straight-chain or branched. It is preferably straight-chain and is particularly preferably 3-oxabut-1-enyl (=methoxyvinyl), 2-oxabut-3-enyl (=vinyloxymethyl), 4-oxapent-1-enyl (=methoxyprop-1-enyl), 3-oxapent-1-enyl (=ethoxyvinyl), 4-oxapent-2-enyl (=methoxyprop-2-enyl), 2-oxapent-3-enyl (=prop-1-enoxymethyl), 2-oxapent-4-enyl (=prop-2-enoxymethyl), 3-oxapent-4-enyl (=vinyloxyethyl), 3-oxahex-1-enyl, 4-oxahex-1-enyl, 5-oxahex-1-enyl, 4-oxahex-2-enyl, 5-oxahex-2-enyl, 2-oxahex-3-enyl, 5-oxahex-3-enyl, 2-oxahex-4-enyl, 3-oxahex-4-enyl, 2-oxahex-5-enyl, 3-oxahex-5-enyl or 4-oxahex-5-enyl.

If $R^1$ and/or $R^2$ are an alkyl radical in which one $CH_2$ group has been replaced by —O— and one has been replaced by —CO—, these are preferably adjacent. This thus contains a carbonyloxy group (acyloxy group) —CO—O— or an oxycarbonyl group —O—CO—. These are preferably straight-chain and have from 2 to 6 carbon atoms. Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)-ethyl, 3-(methoxycarbonyl) propyl, 3-(ethoxycarbonyl)propyl or 4-(methoxycarbonyl) butyl.

Compounds of the formula I having a branched wing group $R^1$ and/or $R^2$ may occasionally be of importance owing to better solubility in the conventional liquid-crystalline base materials, but in particular as chiral dopants if they are optically active. Smectic compounds of this type are particularly suitable as components of ferroelectric materials.

Branched groups of this type generally contain not more than one chain branch. Preferred chiral branched radicals $R^1$ and/or $R^2$ are 2-butyl (=1-methylpropyl), 2-methylbutyl, 2-methylpentyl, 3-methylpentyl, 2-ethylhexyl, 2-propylpentyl, 2-octyl, in particular 2-methylbutyl, 2-methylbutoxy, 2-methylpentoxy, 3-methylpentoxy, 2-ethylhexoxy, 1-methylhexoxy, 1-methylheptyloxy, 2-octyloxy, 2-oxa-3-methylbutyl, 3-oxa-4-methylpentyl, 4-methylhexyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy.

Preferred achiral branched radicals $R^1$ and/or $R^2$ are isopropyl, isobutyl (=2-methylpropyl), isopentyl (=3-methylbutyl), isopropoxy, 2-methylpropoxy and 3-methylbutoxy.

The formula I covers both the racemates of these compounds and the optical antipodes, and mixtures thereof.

In the case of the above-mentioned meanings of $R^1$ and $R^2$, in particular as alkyl, alkenyl, alkoxy, alkenyloxy, oxaalkyl, oxaalkenyl, alkylcarbonyloxy or alkyloxycarbonyl, one or more H atoms have preferably been replaced by halogen atoms, preferably by fluorine and/or chlorine, particularly preferably by fluorine. Preferably, 2 or more H atoms have been substituted by fluorine. Particularly preferably, 2 or 3 H atoms in the terminal methyl group in the above-mentioned radicals have been substituted by fluorine, so that the above-mentioned radicals contain a —$CHF_2$ or a —$CF_3$ group. The entire radical $R^1$ and/or $R^2$ can also be perfluorinated.

Of the compounds of the formula I and the sub-formulae, preference is given to those in which at least one of the radicals present therein has one of the preferred meanings indicated.

The compounds according to the invention are prepared by methods known per se from the literature, as described in the standard works on organic synthesis, for example Houben-Weyl, Methoden der Organischen Chemie [Methods of Organic Chemistry], Georg-Thieme-Verlag, Stuttgart. The preparation is carried out here under reaction conditions which are known and suitable for the said reactions. Use can also be made here of synthetic variants which are known per se, but are not mentioned here in greater detail. The starting materials and/or intermediates can also, if necessary, be formed in situ, i.e. they are not isolated from the reaction mixture, but instead immediately converted further.

The synthesis of three compounds of the formulae Ia-W1, Ia-W2 and Ia-W3 according to the invention starting from the fluorenone compound of the formula IIa is indicated by way of example with reference to reaction scheme 1. The formation of the compound Ia-W1 is carried out using a suitable reducing agent, such as, for example, $NaBH_4$, in the presence of $AlCl_3$ and tetrahydrofuran (THF) as solvent.

In the synthesis of compounds of the formula Ia-W2, a reduction is carried out first, followed by a fluorination, for example using NaBH₄ and subsequently diethylaminosulfur trifluoride (DAST). A further possible synthesis proceeds in two steps via a phenyl sulfide. The carbonyl compound (here the fluorenone) is firstly reacted with phenylthiol with catalysis by boron trifluoride monohydrate and subsequently reduced using triethylsilane. In the second step, the phenyl sulfide obtained is fluorinated using nitrosonium tetrafluoroborate/pyridine/HF complex (Ch. York et al., Tetrahedron 52, 1996, 9–14).

In order to prepare the 9,9-difluorofluorenes of the formula Ia-W3, firstly the fluorenone compound of the formula IIa is converted into the corresponding dithioketal, for example by reaction with ethane-1,2-dithiol in the presence of boron trifluoride. The dithioketal is subsequently subjected to oxidative fluorodesulfurisation in the presence of a fluorinating agent and an oxidant. The oxidant employed is preferably a compound which liberates halonium equivalents. Illustrative oxidants are N-bromosuccinimide, N-iodosuccinimide, 1,3-dibromo-5,5-dimethylhydantoin and bromine. Also suitable are, for example, SO₂Cl₂, SO₂ClF, nitrosonium and nitronium salts (C. York in loco citato) and chloramine T. The nitrosonium and nitronium salts can also, if desired, be prepared in situ from suitable precursors, for example from inorganic or organic nitrites and/or nitrates. Fluorinating agents which can be employed are conventional fluorinating agents. The fluorinating agent is particularly preferably selected from the group formed by aliphatic and aromatic amine/hydrogen fluoride complexes, such as, for example, pyridine/hydrogen fluoride complexes, NEt₃·3HF, melamine/HF and polyvinylpyridine/HF.

The reaction conditions to be observed in the said reactions are known per se to the person skilled in the art. In general, the reaction is carried out at a temperature of from −100 to +50° C. As solvent, use is made of inert polar solvents or mixtures thereof, for example ethers or haloalkanes, such as diethyl ether, tetrahydrofuran or dichloromethane.

A suitable synthetic route for the preparation of the fluorenones of the formula IIa is indicated in reaction scheme 2. According to this, the synthesis is carried out starting from the brominated aromatic compound of the formula Va via the corresponding boron compound IVa and cross-coupling thereof with the brominated aromatic compound of the formula Va' to give the biphenyl compound of the formula IIIa, which is reacted with dimethyl carbonate to give the fluorenone (R. D. Chamber et al., JCS (C) 1968, 2394).

In the reaction schemes 1 and 2, R¹, R², L¹ and L² are as defined above. The syntheses described are suitable not only for compounds of the formula Ia, which have been selected here for reasons of clarity, but also for all compounds of the formula I according to the invention.

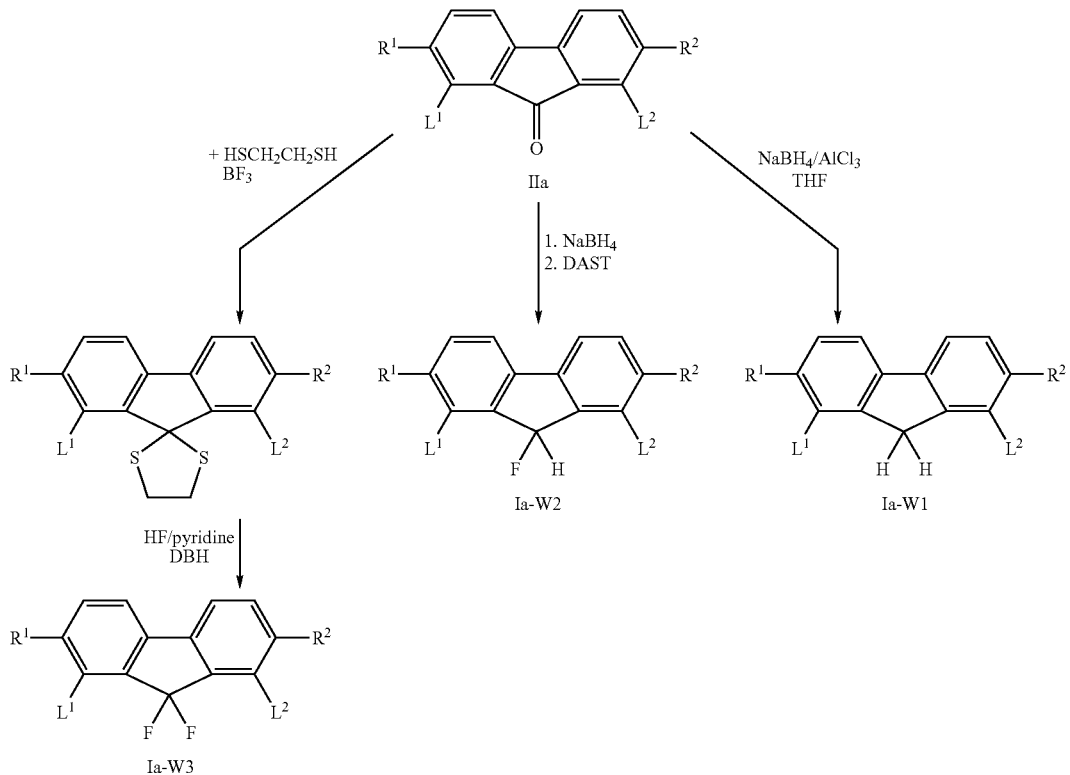

Reaction scheme 1

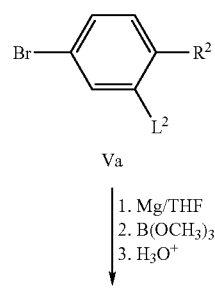

Reaction scheme 2

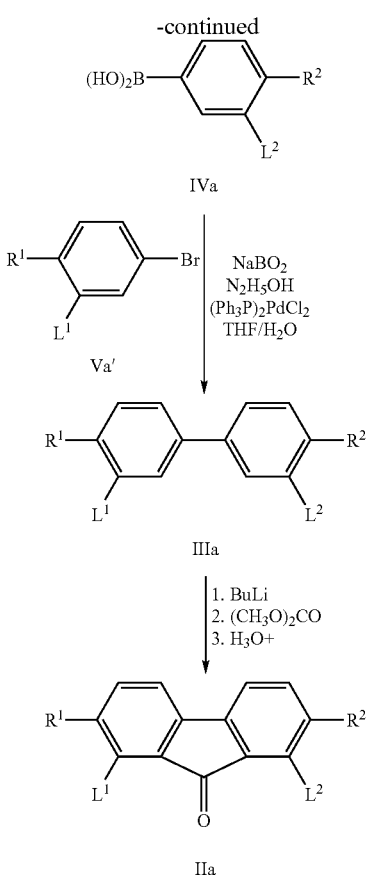

Further suitable possible syntheses can be obtained by the person skilled in the art by analogous use of the syntheses described in reaction schemes 1 to 8 of DE 197 20 289 A1.

Esters of the formula I can also be obtained by esterification of corresponding carboxylic acids (or reactive derivatives thereof using alcohols or phenols (or reactive derivatives thereof or by the DCC method (DCC=dicyclohexylcarbodiimide).

The corresponding carboxylic acids and alcohols are known or can be prepared analogously to known processes.

Suitable reactive derivatives of the said carboxylic acids are in particular the acid halides, especially the chlorides and bromides, furthermore the anhydrides, azides or esters, in particular alkyl esters having 1–4 carbon atoms in the alkyl group.

Suitable reactive derivatives of the said alcohols are, in particular, the corresponding metal alkoxides, preferably of an alkali metal, such as Na or K.

The esterification is advantageously carried out in the presence of an inert solvent. Highly suitable solvents are, in particular, ethers, such as diethyl ether, di-n-butyl ether, THF, dioxane and anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane or tetrachloroethylene, and sulfoxides, such as dimethyl sulfoxide or sulfolane. Water-immiscible solvents may advantageously be used at the same time for azeotropic removal by distillation of the water formed during the esterification. An excess of an organic base, for example pyridine, quinoline or triethylamine, may occasionally also be used as solvent for the esterification. The esterification may also be carried out in the absence of a solvent, for example by simple heating of the components in the presence of sodium acetate. The reaction temperature is usually between −50° C. and +250° C., preferably between −20° C. and +80° C. At these temperatures, the esterification reactions are generally complete after from 15 minutes to 48 hours.

In detail, the reaction conditions for the esterification depend substantially on the nature of the starting materials used. Thus, a free carboxylic acid is generally reacted with a free alcohol in the presence of a strong acid, for example a mineral acid, such as hydrochloric acid or sulfuric acid. A preferred reaction procedure is the reaction of an acid anhydride or in particular an acid chloride with an alcohol, preferably in a basic medium, important bases being, in particular, alkali metal hydroxides, such as sodium hydroxide or potassium hydroxide, alkali metal carbonates or hydrogencarbonates, such as sodium carbonate, sodium hydrogencarbonate, potassium carbonate or potassium hydrogencarbonate, alkali metal acetates, such as sodium acetate or potassium acetate, alkaline earth metal hydroxides, such as calcium hydroxide, or organic bases, such as triethylamine, pyridine, lutidine, collidine or quinoline. A further preferred embodiment of the esterification comprises firstly converting the alcohol into the sodium alkoxide or potassium alkoxide, for example by treatment with ethanolic sodium hydroxide solution or potassium hydroxide solution, isolating this alkoxide, and reacting it with an acid anhydride or in particular an acid chloride.

In a further process for the preparation of the compounds of the formula I in which $Z^1$, $Z^2$, $Z^3$ or $Z^4$ is —CH═CH—, an aryl halide is reacted with an olefin in the presence of a tertiary amine and in the presence of a palladium catalyst (cf. R. F. Heck, Acc. Chem. Res. 12 (1979) 146). Examples of suitable aryl halides are chlorides, bromides and iodides, in particular bromides and iodides. The tertiary amines necessary for the success of the coupling reaction, such as, for example, triethylamine, are also suitable as solvent. Examples of suitable palladium catalysts are the salts thereof, in particular Pd(II) acetate, with organic phosphorus (III) compounds, such as, for example, triarylphosphines. The process can be carried out in the presence or absence of an inert solvent at temperatures between about 0° C. and 150° C., preferably between 20° C. and 100° C.; suitable solvents are, for example, nitriles, such as acetonitrile, or hydrocarbons, such as benzene or toluene. The aryl halides and olefins employed as starting materials are in many cases commercially available or can be prepared by processes known from the literature, for example by halogenation of corresponding parent compounds or by elimination reactions on corresponding alcohols or halides.

In this way, stilbene derivatives, for example, can be prepared. The stilbenes can furthermore be prepared by reaction of a 4-substituted benzaldehyde with a corresponding phosphorus ylide by the Wittig method. However, tolans of the formula I can also be prepared by employing monosubstituted acetylene instead of the olefin (Synthesis 627 (1980) or Tetrahedron Lett. 27, 1171 (1986)).

For the coupling of aromatic compounds, it is furthermore possible to react aryl halides with aryltin compounds. These reactions are preferably carried out with addition of a catalyst, such as, for example, a palladium(0) complex, in inert solvents, such as hydrocarbons, at high temperatures, for example in boiling xylene, under a protective gas.

Coupling reactions of alkynyl compounds with aryl halides can be carried out analogously to the process described by A. O. King, E. Negishi, F. J. Villani and A. Silveira in J. Org. Chem. 43, 358 (1978).

Tolans of the formula I in which $Z^1$, $Z^2$, $Z^3$ or $Z^4$ is —C≡C— can also be prepared by the Fritsch-buttenberg-Wiechell rearrangement (Ann. 279, 319, 1984), in which 1,1-diaryl-2-haloethylenes are rearranged to give diarylacetylenes in the presence of strong bases.

Tolans of the formula I can also be prepared by brominating the corresponding stilbenes, followed by dehydrohalogenation. Use can be made here of variants of this reaction which are known per se, but are not mentioned here in greater detail.

Ethers of the formula I are obtainable by etherification of corresponding hydroxyl compounds, preferably corresponding phenols, where the hydroxyl compound is advantageously firstly converted into a corresponding metal derivative, for example into the corresponding alkali metal alkoxide or alkali metal phenoxide by treatment with NaH, $NaNH_2$, NaOH, KOH, $Na_2CO_3$ or $K_2CO_3$. This metal derivative can then be reacted with the appropriate alkyl halide, alkyl sulfonate or dialkyl sulfate, advantageously in an inert solvent, such as, for example, acetone, 1,2-dimethoxyethane, DMF or dimethyl sulfoxide, or alternatively with an excess of aqueous or aqueous-alcoholic NaOH or KOH, at temperatures between about 20° C. and 100° C.

In order to prepare the laterally substituted fluorine or chlorine compounds of the formula I, corresponding aniline derivatives can be reacted with sodium nitrite and either with tetrafluoroboric acid (in order to introduce an F atom) or with copper(I) chloride (in order to introduce a Cl atom) to give the diazonium salts, which are then thermally decomposed at temperatures of 100–140° C.

The linking of an aromatic ring to a non-aromatic ring or of two non-aromatic rings is preferably obtained by condensation of an organolithium or organomagnesium compound with a ketone if an aliphatic group $Z^1$ is intended to be present between the rings.

The organometallic compounds are prepared, for example, by metal-halogen exchange (for example in accordance with Org. React. 6, 339–366 (1951)) between the corresponding halogen compound and an organo-lithium compound, preferably tert-butyllithium or lithium naphthalenide, or by reaction with magnesium turnings.

The linking of two aromatic rings is preferably carried out by Friedel-Crafts alkylation or acylation by reacting the corresponding aromatic compounds with Lewis acid catalysis. Suitable Lewis acids are, for example, $SnCl_4$, $ZnCl_2$, $AlCl_3$ and $TiCl_4$.

Furthermore, the linking of two aromatic rings can be carried out by the Ullmann reaction (for example Synthesis 1974, 9) between aryl iodides and copper iodide, but preferably between an arylcopper compound and an aryl iodide, or by the Gomberg-Bachmann reaction between an aryldiazonium salt and the corresponding aromatic compound (for example Org. React. 2, 224 (1944)).

The tolans of the formula I are prepared, for example, by reaction of the corresponding aryl halides with an acetylide in a basic solvent with transition-metal catalysis; palladium catalysts can preferably be used here, in particular a mixture of bis(triphenylphosphine)palladium(II) chloride and copper iodide in piperidine as solvent.

In addition, the compounds of the formula I can be prepared by reducing a compound which conforms to the formula I, but contains one or more reducible groups and/or C—C bonds in place of H atoms.

Suitable reducible groups are preferably carbonyl groups, in particular keto groups, furthermore, for example, free or esterified hydroxyl groups or aromatically bound halogen atoms. Preferred starting materials for the reduction are compounds conforming to the formula I, but which contain a cyclohexene ring or cyclohexanone ring instead of a cyclohexane ring and/or contain a —$CH_2CH_2$— group instead of a —CH═CH— group and/or contain a —CO— group instead of a —$CH_2$— group and/or contain a free or functionally (for example in the form of its p-toluenesulfonate) modified OH group instead of an H atom.

The reduction can be carried out, for example, by catalytic hydrogenation at temperatures between about 0° C. and about 200° C. and pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are advantageously noble metals, such as Pt or Pd, which can be employed in the form of oxides (for example $PtO_2$ or PdO), on a support (for example Pd on carbon, calcium carbonate or strontium, carbonate) or in finely divided form.

Ketones can also be reduced to the corresponding compounds of the formula I containing alkyl groups and/or —$CH_2CH_2$— bridges by the methods of Clemmensen (using zinc, zinc amalgam or tin and hydrochloric acid, advantageously in aqueous-alcoholic solution or in the heterogeneous phase with water/toluene at temperatures between about 80 and 120° C.) or Wolff-Kishner (using hydrazine, advantageously in the presence of alkali, such as KOH or NaOH, in a high-boiling solvent, such as diethylene glycol or triethylene glycol, at temperatures between about 100 and 200° C.).

Furthermore, reductions with complex hydrides are possible. For example, arylsulfonyloxy groups can be removed reductively using $LiAlH_4$, in particular p-toluenesulfonyloxymethyl groups can be reduced to methyl groups, advantageously in an inert solvent, such as diethyl ether or THF, at temperatures between about 0 and 100° C. Double bonds can be hydrogenated using $NaBH_4$ or tributyltin hydride in methanol.

The starting materials are either known or can be prepared analogously to known compounds.

The liquid-crystalline media according to the invention preferably comprise from 2 to 40, in particular from 4 to 30, components as further constituents besides one or more compounds according to the invention. These media very particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid or of cyclohexylcyclohexanecarboxylic acid, phenylcyclohexanes, cyclohexylbiphenyls, phenylcyclohexylcyclohexanes, cyclohexylcyclohexanes, cyclohexylcyclohexylcyclohexenes, 1,4-biscyclohexylbenzenes, 4,4'-biscyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl- 2-(4-phenyl-cyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further constituents of media according to the invention can be characterised by the formulae 1, 2, 3, 4 and 5:

R'—L—E—R''  1

R'—L—COO—E—R''  2

R'—L—OOC—E—R''  3

R'—L—CH$_2$CH$_2$—E—R''  4

R'—L—C≡C—E—R''  5

In the formulae 1, 2, 3, 4 and 5, L and E, which may be identical or different, are each, independently of one another, a divalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, cyc is trans-1,4-cyclohexylene or 1,4-cyclohexenylene, Pyr is pyrimidine-2,5-diyl or pyridine-2,5-diyl, Dio is 1,3-dioxane-2,5-diyl, and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

R' and/or R'' are each, independently of one another, alkyl, alkenyl, alkoxy, alkoxyalkyl, alkenyloxy or alkanoyloxy having up to 8 carbon atoms, —F, —Cl, —CN, —NCS or —(O)$_i$CH$_{3-(k+l)}$F$_k$Cl$_l$, where i is 0 or 1 and k and l are 1, 2 or 3.

In a smaller sub-group of the compounds of the formulae 1, 2, 3, 4 and 5, R' and R'' are each, independently of one another, alkyl, alkenyl, alkoxy, alkoxyalkyl, alkenyloxy or alkanoyloxy having up to 8 carbon atoms. This smaller sub-group is called group A below, and the compounds are referred to by the sub-formulae 1a, 2a, 3a, 4a and 5a. In most of these compounds, R' and R'' are different from one another, one of these radicals usually being alkyl, alkenyl, alkoxy or alkoxyalkyl.

In another smaller sub-group of the compounds of the formulae 1, 2, 3, 4 and 5, which is known as group B, R'' is —F, —Cl, —NCS or —(O)$_i$CH$_{3-(k+l)}$F$_k$Cl$_l$, where i is 0 or 1, and k and l are 1, 2 or 3; the compounds in which R'' has this meaning are referred to by the sub-formulae 1b, 2b, 3b, 4b and 5b. Particular preference is given to those compounds of the sub-formulae 1b, 2b, 3b, 4b and 5b in which R'' is —F, —Cl, —NCS, —CF$_3$, —OCHF$_2$ or —OCF$_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller sub-group of the compounds of the formulae 1, 2, 3, 4 and 5, R'' is —CN; this sub-group is referred to below as group C, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

Besides the preferred compounds of groups A, B and C, other compounds of the formulae 1, 2, 3, 4 and 5 having other variants of the proposed substituents are also customary. all these substances are obtainable by methods which are known from the literature or analogously thereto.

Besides the compounds of the formula I according to the invention, the media according to the invention preferably comprise one or more compounds selected from group A and/or group B and/or group C. The proportions by weight of the compounds from these groups in the media according to the invention are preferably group A: from 0 to 90%, preferably from 20 to 90%, in particular from 30 to 90% group B: from 0 to 80%, preferably from 10 to 80%, in particular from 10 to 65% group C: from 0 to 80%, preferably from 5 to 80%, in particular from 5 to 50%, the sum of the proportions by weight of the group A and/or B and/or C compounds present in the respective media according to the invention preferably being 5% to 90% and in particular from 10% to 90%.

The media according to the invention preferably comprise from 1 to 40%, particularly preferably from 5 to 30%, of the compounds according to the invention. Preference is furthermore given to media comprising more than 40%, in particular from 45 to 90%, of compounds according to the invention. The media preferably comprise three, four or five compounds according to the invention.

The liquid-crystal mixtures which can be used in accordance with the invention are prepared in a manner conventional per se. In general, the desired amount of the components used in the lesser amount is dissolved in the components making up the principal constituent, advantageously at elevated temperature. It is also possible to mix solutions of the components in an organic solvent, for example in acetone, chloroform or methanol, and to remove the solvent again, for example by distillation, after thorough mixing. It is furthermore possible to prepare the mixtures in other conventional manners, for example by using premixes, for example homologue mixtures, or using so-called "multi-bottle" systems.

The dielectrics may also comprise further additives known to the person skilled in the art and described in the literature. For example, 0–15%, preferably 0–10%, of pleochroic dyes and/or chiral dopants can be added. The individual compounds added are employed in concentrations of from 0.01 to 6%, preferably from 0.1 to 3%. However, the concentration figures for the other constituents of the liquid-crystal mixtures, i.e. of the liquid-crystalline or mesogenic compounds, are indicated without taking into account the concentration of these additives.

The following examples are intended to explain the invention without limiting it. Above and below, percentages are per cent by weight. All temperatures are given in degrees Celsius.

"Conventional work-up" means that water is added if desired, the mixture is extracted with methylene chloride, diethyl ether or toluene, the phases are separated, the organic phase is dried and evaporated, and the product is purified by distillation under reduced pressure or crystallisation and/or chromatography.

WORKING EXAMPLES

1. Synthesis of 2-butoxy-7-ethoxy-1,8,9,9-tetrafluorofluorene of the formula 8

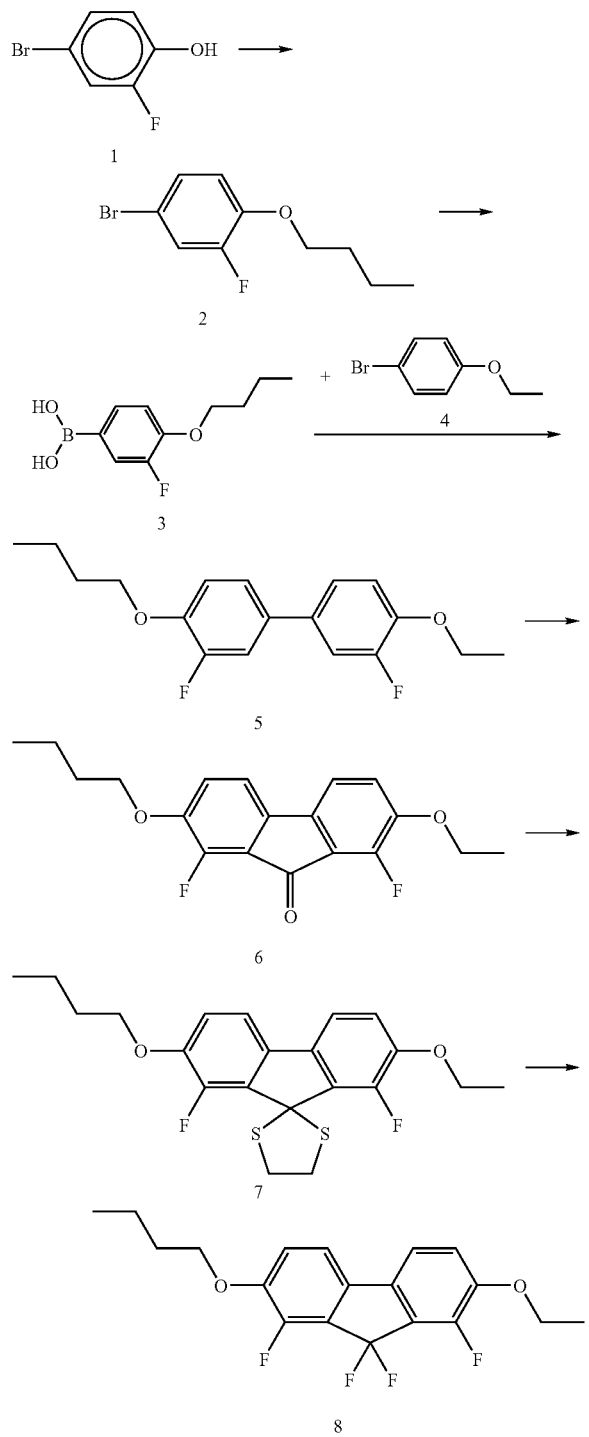

1.1 Preparation of 1-bromo-3-fluoro-4-butoxybenzene (2)

0.315 mol of each of 4-bromo-2-fluorophenol (1), 1-butanol and triphenylphosphine were dissolved in 1000 ml of tetrahydrofuran, and 0.315 mol of diisopropyl azodicarboxylate was added dropwise at about 20° C. After the mixture had been stirred overnight, the solvent was removed by distillation in a rotary evaporator, and the residue was subjected to conventional work-up, giving the compound (2) in a yield of 95.6% of theory.

1.2 Preparation of the Boron Compound (3)

0.180 mol of n-butyllithium (as a 15% solution in n-hexane) was added dropwise at −70° C. to a solution of 0.162 mol of 1-bromo-3-fluoro-4-butoxybenzene (2) in 540 ml of diethyl ether. After the mixture had been stirred for 30 minutes, 0.180 mol of trimethyl borate was added dropwise at −70° C., and the mixture was stirred for a further 30 minutes. The reaction mixture warmed to 20° C. was hydrolysed with water and acidified with 2 molar hydrochloric acid, and methyl tert-butyl ether was added. The mixture was subjected to conventional work-up, giving the compound (3) as a white solid.

1.3 Cross-coupling to give 4-ethoxy-3,3'-difluoro-4'-butoxybiphenyl (5)

10 ml of tetrahydrofuran, 0.628 mmol of bis(triphenylphosphine)palladium dichloride and 0.630 mmol of hydrazinium hydroxide were added to 24.1 mmol of sodium metaborate octahydrate in 12.6 ml of $H_2O$, and the mixture was stirred at room temperature for 5 minutes. 32.1 mmol of the boron compound (3), 32.1 mmol of 1-bromo-3-fluoro-4-ethoxybenzene (4) (prepared analogously to Example 1.1) and 30 ml of tetrahydrofuran were then added, and the mixture was heated under reflux conditions for 6 hours. After subsequent cooling, the organic phase was separated off and subjected to conventional work-up.

1.4 Preparation of the Fluorenone Derivative (6)

60 mmol of 4-ethoxy-3,3'-difluoro-4'-butoxybiphenyl (5) are introduced into 200 ml of tetrahydrofuran, and the mixture is cooled to −70° C. 120 mmol of a 1.6 M solution of n-butyllithium in hexane are added dropwise, and the mixture is stirred at this temperature for 2 hours. 60 mmol of dimethyl carbonate are subsequently added rapidly with vigorous stirring, the mixture is stirred at −70° C. for a further hour, allowed to warm to 0° C., hydrolysed with dilute hydrochloric acid and subjected to conventional work-up.

1.5 Preparation of the Dithioketal Compound (7)

30 mmol of the fluorenone derivative (6) are dissolved in 100 ml of diethyl ether, 60 mmol of 1,2-ethanediol and 45 mmol of boron trifluoride etherate are added, and the mixture is heated overnight under reflux conditions. After cooling, the mixture is subjected to conventional work-up, giving 27.5 mmol (92%) of the dithioketal (7).

1.6 Oxidative Fluorodesulfurisation to Give the Fluorene Derivative (8)

11 mmol of 1,3-dibromo-5,5-dimethylhydantoin are dissolved in 50 ml of dichloromethane, and the mixture is cooled to −70° C. 29 mmol of hydrogen fluoride in pyridine (65%) are added. 11 mmol of the dithioketal (7) dissolved in 50 ml of dichloromethane are added dropwise over the course of 20 minutes, and the mixture is allowed to warm to −60° C. after one hour. The reaction mixture is poured into saturated sodium hydrogencarbonate solution and then subjected to conventional work-up, giving the fluorene derivative (8). ($\Delta\epsilon=-21.2$, $\Delta n=0.204$).

For comparison, measurements are made on the difluorinated compound 2-butoxy-7-ethoxy-9,9-difluorofluorene obtainable analogously: $\Delta\epsilon=-9.1$, $\Delta n=0.225$.

2. Synthesis of 2-butoxy-7-ethoxy-1,8,9-trifluoro-9H-fluorene of the formula 9

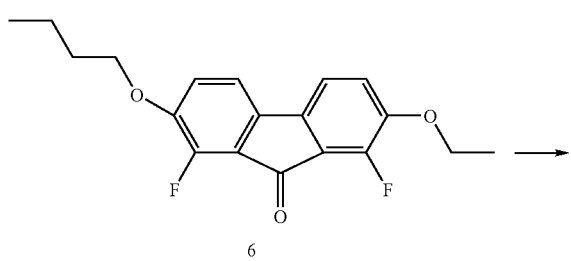

20 mmol of the fluorenone compound (6) (obtainable in accordance with Example 1.4) are dissolved in 100 ml of isopropanol, and 8 mmol of sodium borohydride are added. The mixture is stirred at room temperature for 3 hours and subjected to conventional work-up. The crude product is dissolved in 300 ml of dichloromethane and cooled to 0° C. 20 mmol of diethylaminosulfur trifluoride are added dropwise, and the mixture is subjected to conventional work-up, giving the 9H-fluorene (9). ($\Delta\epsilon=-15.3$, $\Delta n=0.214$).

For comparison, measurements are made on the monofluorinated compound 2-butoxy-7-ethoxy-9-fluoro-9H-fluorene obtainable analogously: $\Delta\epsilon=-4.7$, $\Delta n=0.238$.

3. Synthesis of 2-butoxy-7-ethoxy-1,8-difluoro-9,9H-fluorene of the formula 10

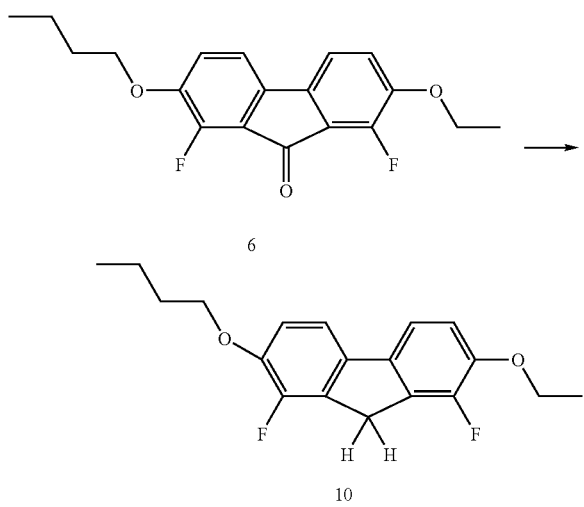

27 mmol of the fluorenone compound (6) (obtainable in accordance with Example 1.4), 13 mmol of sodium borohydride and 74 mmol of aluminium chloride are suspended in 250 ml of tetrahydrofuran, and the mixture is heated under reflux conditions for 2 hours. Conventional work-up gives 23.4 mmol (87%) of the 9,9H-fluorene (10). ($\Delta\epsilon=-8.7$, $\Delta n=0.226$).

For comparison, measurements are made on the unfluorinated compound 2-butoxy-7-ethoxy-9,9H-fluorene obtainable analogously: $\Delta\epsilon=-0.5$, $\Delta n=0.253$.

4. Synthesis of the 1,8,9,9-tetrafluorofluorene compound of the formula 20

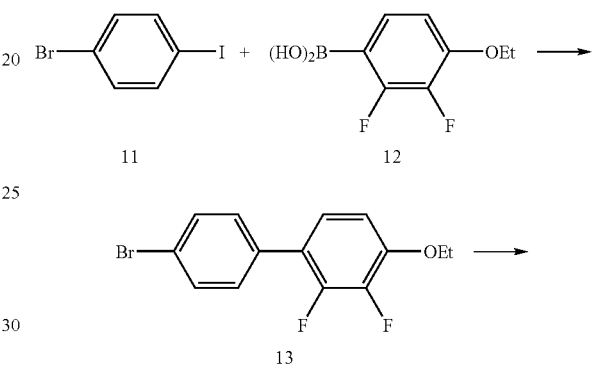

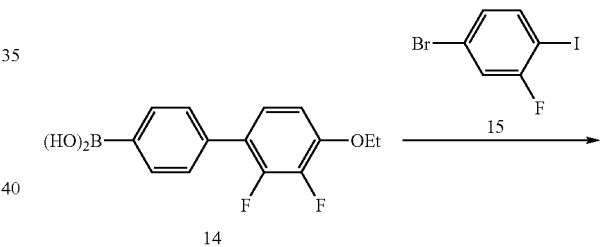

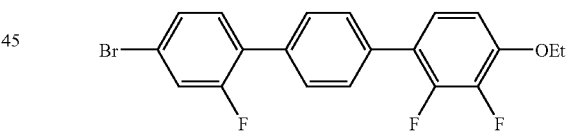

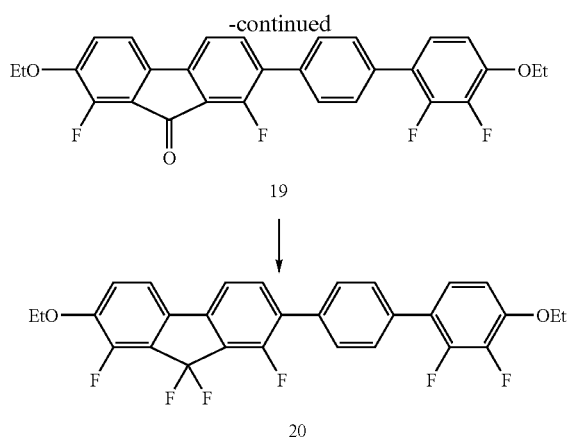

4.1 Preparation of 1-bromo-2',3'-difluoro-4'-ethoxybiphenyl (13)

0.450 mol of sodium metaborate are introduced into 240 ml of water. 0.012 mol of bis(triphenylphosphine)palladium (II) chloride, 0.6 mol of 4-bromo-1-iodobenzene (11) and 0.012 mol of hydrazinium hydrochloride are added, and the mixture is stirred at about 20° C. for 5 minutes. 0.6 mol of 2,3-difluoro-4-ethoxyphenylboronic acid (12) dissolved in 600 ml of tetrahydrofuran are then added, and the mixture is refluxed for 4 hours, giving the compound of the formula 13.

4.2 Preparation of the Boronic Acid Compound (14)

0.09 mol of 1-bromo-2',3'-difluoro-4'-ethoxybiphenyl (13) is dissolved in 200 ml of diethyl ether, and the mixture is cooled to −70° C. 0.095 mol of butyllithium is added dropwise at this temperature, and the mixture is stirred for a further 45 minutes. 0.1 mol of trimethyl borate is then added, and the mixture is stirred for 30 minutes and, after warming to about 20° C., subjected to conventional work-up.

4.3 Preparation of the Terphenyl Compound (16)

0.047 mol of 2',3'-difluoro-4'-ethoxybiphenylboronic acid (14), 0.05 mol of 1-bromo-3-fluoro-4-iodobenzene (15), 1 mmol of palladium acetate, 2 mmol of triphenylphosphine, 25 ml of saturated sodium carbonate solution, 20 ml of water and 100 ml of isopropanol are initially introduced and refluxed overnight. Conventional work-up gives the terphenyl compound (16).

4.4 Preparation of the Compound of the Formula 18

The preparation is carried out analogously to Example 1.3 using the terphenyl compound (16) and 3-fluoro-4-ethoxyphenylboronic acid (17).

4.5 Preparation of the Fluorenone Compound (19)

The synthesis is carried out analogously to Example 1.4 using the compound (18) obtained previously.

4.6 Preparation of the 1,8,9,9-tetrafluorofluorene compound (20)

The compound (20) is obtained in the final step analogously to Examples 1.5 and 1.6 by oxidative fluorodesulfurisation of the compound (19) (Δε=−28.8, Δn 0.282).

Fluorene compounds of the following formula

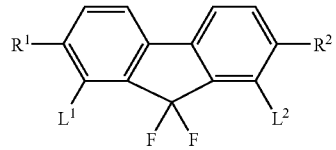

are obtained analogously to Examples 1.1 to 1.6, in particular 1.5 and 1.6:

| | $R^1$ | $R^2$ | $L^1$ | $L^2$ |
|---|---|---|---|---|
| (21) | —$C_3H_7$ | —$C_3H_7$ | —H | —F |
| (22) | —$C_3H_7$ | —$C_4H_9$ | —H | —F |
| (23) | —$C_3H_7$ | —$C_5H_{11}$ | —H | —F |
| (24) | —$C_3H_7$ | —$OC_2H_5$ | —H | —F |
| (25) | —$C_3H_7$ | —$OC_3H_7$ | —H | —F |
| (26) | —$C_3H_7$ | —$OC_4H_9$ | —H | —F |
| (27) | —$C_3H_7$ | —$OC_5H_{11}$ | —H | —F |
| (28) | —$C_4H_9$ | —$C_3H_7$ | —H | —F |
| (29) | —$C_4H_9$ | —$C_4H_9$ | —H | —F |
| (30) | —$C_4H_9$ | —$C_5H_{11}$ | —H | —F |
| (31) | —$C_4H_9$ | —$OC_2H_5$ | —H | —F |
| (32) | —$C_4H_9$ | —$OC_3H_7$ | —H | —F |
| (33) | —$C_4H_9$ | —$OC_4H_9$ | —H | —F |
| (34) | —$C_4H_9$ | —$OC_5H_{11}$ | —H | —F |
| (35) | —$C_5H_{11}$ | —$C_3H_7$ | —H | —F |
| (36) | —$C_5H_{11}$ | —$C_4H_9$ | —H | —F |
| (37) | —$C_5H_{11}$ | —$C_5H_{11}$ | —H | —F |
| (38) | —$C_5H_{11}$ | —$OC_2H_5$ | —H | —F |
| (39) | —$C_5H_{11}$ | —$OC_3H_7$ | —H | —F |
| (40) | —$C_5H_{11}$ | —$OC_4H_9$ | —H | —F |
| (41) | —$C_5H_{11}$ | —$OC_5H_{11}$ | —H | —F |
| (42) | —CH=$CH_2$ | —$C_3H_7$ | —H | —F |
| (43) | —CH=$CH_2$ | —$C_4H_9$ | —H | —F |
| (44) | —CH=$CH_2$ | —$C_5H_{11}$ | —H | —F |
| (45) | —CH=$CH_2$ | —CH=$CH_2$ | —H | —F |
| (46) | —CH=$CH_2$ | —CH=CH—$CH_3$ | —H | —F |
| (47) | —CH=$CH_2$ | —$CH_2$—CH=CH—$CH_3$ | —H | —F |
| (48) | —CH=$CH_2$ | —$C_2H_4$—CH=$CH_2$ | —H | —F |
| (49) | —CH=$CH_2$ | —$C_2H_4$—CH=CH—$CH_3$ | —H | —F |
| (50) | —CH=$CH_2$ | —$OC_2H_5$ | —H | —F |

-continued

| | R¹ | R² | L¹ | L² |
|---|---|---|---|---|
| (51) | —CH=CH₂ | —OC₃H₇ | —H | —F |
| (52) | —CH=CH₂ | —OC₄H₉ | —H | —F |
| (53) | —CH=CH₂ | —OC₅H₁₁ | —H | —F |
| (54) | —CH=CH—CH₃ | —C₃H₇ | —H | —F |
| (55) | —CH=CH—CH₃ | —C₄H₉ | —H | —F |
| (56) | —CH=CH—CH₃ | —C₅H₁₁ | —H | —F |
| (57) | —CH=CH—CH₃ | —CH=CH₂ | —H | —F |
| (58) | —CH=CH—CH₃ | —CH=CH—CH₃ | —H | —F |
| (59) | —CH=CH—CH₃ | —CH₂—CH=CH—CH₃ | —H | —F |
| (60) | —CH=CH—CH₃ | —C₂H₄—CH=CH₂ | —H | —F |
| (61) | —CH=CH—CH₃ | —C₂H₄—CH=CH—CH₃ | —H | —F |
| (62) | —CH=CH—CH₃ | —OC₂H₅ | —H | —F |
| (63) | —CH=CH—CH₃ | —OC₃H₇ | —H | —F |
| (64) | —CH=CH—CH₃ | —OC₄H₉ | —H | —F |
| (65) | —CH=CH—CH₃ | —OC₅H₁₁ | —H | —F |
| (66) | —CH₂—CH=CH—CH₃ | —C₃H₇ | —H | —F |
| (67) | —CH₂—CH=CH—CH₃ | —C₄H₉ | —H | —F |
| (68) | —CH₂—CH=CH—CH₃ | —C₅H₁₁ | —H | —F |
| (69) | —CH₂—CH=CH—CH₃ | —CH=CH₂ | —H | —F |
| (70) | —CH₂—CH=CH—CH₃ | —CH=CH—CH₃ | —H | —F |
| (71) | —CH₂—CH=CH—CH₃ | —CH₂—CH=CH—CH₃ | —H | —F |
| (72) | —CH₂—CH=CH—CH₃ | —C₂H₄—CH=CH₂ | —H | —F |
| (73) | —CH₂—CH=CH—CH₃ | —C₂H₄—CH=CH—CH₃ | —H | —F |
| (74) | —CH₂—CH=CH—CH₃ | —OC₂H₅ | —H | —F |
| (75) | —CH₂—CH=CH—CH₃ | —OC₃H₇ | —H | —F |
| (76) | —CH₂—CH=CH—CH₃ | —OC₄H₉ | —H | —F |
| (77) | —CH₂—CH=CH—CH₃ | —OC₅H₁₁ | —H | —F |
| (78) | —C₂H₄—CH=CH₂ | —C₃H₇ | —H | —F |
| (79) | —C₂H₄—CH=CH₂ | —C₄H₉ | —H | —F |
| (80) | —C₂H₄—CH=CH₂ | —C₅H₁₁ | —H | —F |
| (81) | —C₂H₄—CH=CH₂ | —CH=CH₂ | —H | —F |
| (82) | —C₂H₄—CH=CH₂ | —CH=CH—CH₃ | —H | —F |
| (83) | —C₂H₄—CH=CH₂ | —CH₂—CH=CH—CH₃ | —H | —F |
| (84) | —C₂H₄—CH=CH₂ | —C₂H₄—CH=CH₂ | —H | —F |
| (85) | —C₂H₄—CH=CH₂ | —C₂H₄—CH=CH—CH₃ | —H | —F |
| (86) | —C₂H₄—CH=CH₂ | —OC₂H₅ | —H | —F |
| (87) | —C₂H₄—CH=CH₂ | —OC₃H₇ | —H | —F |
| (88) | —C₂H₄—CH=CH₂ | —OC₄H₉ | —H | —F |
| (89) | —C₂H₄—CH=CH₂ | —OC₅H₁₁ | —H | —F |
| (90) | —C₂H₄—CH=CH—CH₃ | —C₃H₇ | —H | —F |
| (91) | —C₂H₄—CH=CH—CH₃ | —C₄H₉ | —H | —F |
| (92) | —C₂H₄—CH=CH—CH₃ | —C₅H₁₁ | —H | —F |
| (93) | —C₂H₄—CH=CH—CH₃ | —CH=CH₂ | —H | —F |
| (94) | —C₂H₄—CH=CH—CH₃ | —CH=CH—CH₃ | —H | —F |
| (95) | —C₂H₄—CH=CH—CH₃ | —CH₂—CH=CH—CH₃ | —H | —F |
| (96) | —C₂H₄—CH=CH—CH₃ | —C₂H₄—CH=CH₂ | —H | —F |
| (97) | —C₂H₄—CH=CH—CH₃ | —C₂H₄—CH=CH—CH₃ | —H | —F |
| (98) | —C₂H₄—CH=CH—CH₃ | —OC₂H₅ | —H | —F |
| (99) | —C₂H₄—CH=CH—CH₃ | —OC₃H₇ | —H | —F |
| (100) | —C₂H₄—CH=CH—CH₃ | —OC₄H₉ | —H | —F |
| (101) | —C₂H₄—CH=CH—CH₃ | —OC₅H₁₁ | —H | —F |
| (102) | —OC₂H₅ | —C₃H₇ | —H | —F |
| (103) | —OC₂H₅ | —C₄H₉ | —H | —F |
| (104) | —OC₂H₅ | —C₅H₁₁ | —H | —F |
| (105) | —OC₂H₅ | —OC₂H₅ | —H | —F |
| (106) | —OC₂H₅ | —OC₃H₇ | —H | —F |
| (107) | —OC₂H₅ | —OC₄H₉ | —H | —F |
| (108) | —OC₂H₅ | —OC₅H₁₁ | —H | —F |
| (109) | —OC₃H₇ | —C₃H₇ | —H | —F |
| (110) | —OC₃H₇ | —C₄H₉ | —H | —F |
| (111) | —OC₃H₇ | —C₅H₁₁ | —H | —F |
| (112) | —OC₃H₇ | —OC₂H₅ | —H | —F |
| (113) | —OC₃H₇ | —OC₃H₇ | —H | —F |
| (114) | —OC₃H₇ | —OC₄H₉ | —H | —F |
| (115) | —OC₃H₇ | —OC₅H₁₁ | —H | —F |
| (116) | —OC₄H₉ | —C₃H₇ | —H | —F |
| (117) | —OC₄H₉ | —C₄H₉ | —H | —F |
| (118) | —OC₄H₉ | —C₅H₁₁ | —H | —F |
| (119) | —OC₄H₉ | —OC₂H₅ | —H | —F |
| (120) | —OC₄H₉ | —OC₃H₇ | —H | —F |
| (121) | —OC₄H₉ | —OC₄H₉ | —H | —F |
| (122) | —OC₄H₉ | —OC₅H₁₁ | —H | —F |
| (123) | —OC₅H₁₁ | —C₃H₇ | —H | —F |
| (124) | —OC₅H₁₁ | —C₄H₉ | —H | —F |
| (125) | —OC₅H₁₁ | —C₅H₁₁ | —H | —F |
| (126) | —OC₅H₁₁ | —OC₂H₅ | —H | —F |
| (127) | —OC₅H₁₁ | —OC₃H₇ | —H | —F |

-continued

| | R¹ | R² | L¹ | L² |
|---|---|---|---|---|
| (128) | —OC₅H₁₁ | —OC₄H₉ | —H | —F |
| (129) | —OC₅H₁₁ | —OC₅H₁₁ | —H | —F |
| (130) | —C₃H₇ | —C₃H₇ | —H | —CF₃ |
| (131) | —C₃H₇ | —C₄H₉ | —H | —CF₃ |
| (132) | —C₃H₇ | —C₅H₁₁ | —H | —CF₃ |
| (133) | —C₃H₇ | —OC₂H₅ | —H | —CF₃ |
| (134) | —C₃H₇ | —OC₃H₇ | —H | —CF₃ |
| (135) | —C₃H₇ | —OC₄H₉ | —H | —CF₃ |
| (136) | —C₃H₇ | —OC₅H₁₁ | —H | —CF₃ |
| (137) | —C₄H₉ | —C₃H₇ | —H | —CF₃ |
| (138) | —C₄H₉ | —C₄H₉ | —H | —CF₃ |
| (139) | —C₄H₉ | —C₅H₁₁ | —H | —CF₃ |
| (140) | —C₄H₉ | —OC₂H₅ | —H | —CF₃ |
| (141) | —C₄H₉ | —OC₃H₇ | —H | —CF₃ |
| (142) | —C₄H₉ | —OC₄H₉ | —H | —CF₃ |
| (143) | —C₄H₉ | —OC₅H₁₁ | —H | —CF₃ |
| (144) | —C₅H₁₁ | —C₃H₇ | —H | —CF₃ |
| (145) | —C₅H₁₁ | —C₄H₉ | —H | —CF₃ |
| (146) | —C₅H₁₁ | —C₅H₁₁ | —H | —CF₃ |
| (147) | —C₅H₁₁ | —OC₂H₅ | —H | —CF₃ |
| (148) | —C₅H₁₁ | —OC₃H₇ | —H | —CF₃ |
| (149) | —C₅H₁₁ | —OC₄H₉ | —H | —CF₃ |
| (150) | —C₅H₁₁ | —OC₅H₁₁ | —H | —CF₃ |
| (151) | —OC₂H₅ | —C₃H₇ | —H | —CF₃ |
| (152) | —OC₂H₅ | —C₄H₉ | —H | —CF₃ |
| (153) | —OC₂H₅ | —C₅H₁₁ | —H | —CF₃ |
| (154) | —OC₂H₅ | —OC₂H₅ | —H | —CF₃ |
| (155) | —OC₂H₅ | —OC₃H₇ | —H | —CF₃ |
| (156) | —OC₂H₅ | —OC₄H₉ | —H | —CF₃ |
| (157) | —OC₂H₅ | —OC₅H₁₁ | —H | —CF₃ |
| (158) | —OC₃H₇ | —C₃H₇ | —H | —CF₃ |
| (159) | —OC₃H₇ | —C₄H₉ | —H | —CF₃ |
| (160) | —OC₃H₇ | —C₅H₁₁ | —H | —CF₃ |
| (161) | —OC₃H₇ | —OC₂H₅ | —H | —CF₃ |
| (162) | —OC₃H₇ | —OC₃H₇ | —H | —CF₃ |
| (163) | —OC₃H₇ | —OC₄H₉ | —H | —CF₃ |
| (164) | —OC₃H₇ | —OC₅H₁₁ | —H | —CF₃ |
| (165) | —OC₄H₉ | —C₃H₇ | —H | —CF₃ |
| (166) | —OC₄H₉ | —C₄H₉ | —H | —CF₃ |
| (167) | —OC₄H₉ | —C₅H₁₁ | —H | —CF₃ |
| (168) | —OC₄H₉ | —OC₂H₅ | —H | —CF₃ |
| (169) | —OC₄H₉ | —OC₃H₇ | —H | —CF₃ |
| (170) | —OC₄H₉ | —OC₄H₉ | —H | —CF₃ |
| (171) | —OC₄H₉ | —OC₅H₁₁ | —H | —CF₃ |
| (172) | —OC₅H₁₁ | —C₃H₇ | —H | —CF₃ |
| (173) | —OC₅H₁₁ | —C₄H₉ | —H | —CF₃ |
| (174) | —OC₅H₁₁ | —C₅H₁₁ | —H | —CF₃ |
| (175) | —OC₅H₁₁ | —OC₂H₅ | —H | —CF₃ |
| (176) | —OC₅H₁₁ | —OC₃H₇ | —H | —CF₃ |
| (177) | —OC₅H₁₁ | —OC₄H₉ | —H | —CF₃ |
| (178) | —OC₅H₁₁ | —OC₅H₁₁ | —H | —CF₃ |
| (179) | —C₃H₇ | —C₃H₇ | —F | —CF₃ |
| (180) | —C₃H₇ | —C₄H₉ | —F | —CF₃ |
| (181) | —C₃H₇ | —C₅H₁₁ | —F | —CF₃ |
| (182) | —C₃H₇ | —OC₂H₅ | —F | —CF₃ |
| (183) | —C₃H₇ | —OC₃H₇ | —F | —CF₃ |
| (184) | —C₃H₇ | —OC₄H₉ | —F | —CF₃ |
| (185) | —C₃H₇ | —OC₅H₁₁ | —F | —CF₃ |
| (186) | —C₄H₉ | —C₃H₇ | —F | —CF₃ |
| (187) | —C₄H₉ | —C₄H₉ | —F | —CF₃ |
| (188) | —C₄H₉ | —C₅H₁₁ | —F | —CF₃ |
| (189) | —C₄H₉ | —OC₂H₅ | —F | —CF₃ |
| (190) | —C₄H₉ | —OC₃H₇ | —F | —CF₃ |
| (191) | —C₄H₉ | —OC₄H₉ | —F | —CF₃ |
| (192) | —C₄H₉ | —OC₅H₁₁ | —F | —CF₃ |
| (193) | —C₅H₁₁ | —C₃H₇ | —F | —CF₃ |
| (194) | —C₅H₁₁ | —C₄H₉ | —F | —CF₃ |
| (195) | —C₅H₁₁ | —C₅H₁₁ | —F | —CF₃ |
| (196) | —C₅H₁₁ | —OC₂H₅ | —F | —CF₃ |
| (197) | —C₅H₁₁ | —OC₃H₇ | —F | —CF₃ |
| (198) | —C₅H₁₁ | —OC₄H₉ | —F | —CF₃ |
| (199) | —C₅H₁₁ | —OC₅H₁₁ | —F | —CF₃ |
| (200) | —CH=CH₂ | —C₃H₇ | —F | —CF₃ |
| (201) | —CH=CH₂ | —C₄H₉ | —F | —CF₃ |
| (202) | —CH=CH₂ | —C₅H₁₁ | —F | —CF₃ |
| (203) | —CH=CH₂ | —CH=CH₂ | —F | —CF₃ |
| (204) | —CH=CH₂ | —CH=CH—CH₃ | —F | —CF₃ |

-continued

| | R¹ | R² | L¹ | L² | |
|---|---|---|---|---|---|
| (205) | —CH=CH₂ | —CH₂—CH=CH—CH₃ | —F | —CF₃ | |
| (206) | —CH=CH₂ | —C₂H₄—CH=CH₂ | —F | —CF₃ | |
| (207) | —CH=CH₂ | —C₂H₄—CH=CH—CH₃ | —F | —CF₃ | |
| (208) | —CH=CH₂ | —OC₂H₅ | —F | —CF₃ | |
| (209) | —CH=CH₂ | —OC₃H₇ | —F | —CF₃ | |
| (210) | —CH=CH₂ | —OC₄H₉ | —F | —CF₃ | |
| (211) | —CH=CH₂ | —OC₅H₁₁ | —F | —CF₃ | |
| (212) | —CH=CH—CH₃ | —C₃H₇ | —F | —CF₃ | |
| (213) | —CH=CH—CH₃ | —C₄H₉ | —F | —CF₃ | |
| (214) | —CH=CH—CH₃ | —C₅H₁₁ | —F | —CF₃ | |
| (215) | —CH=CH—CH₃ | —CH=CH₂ | —F | —CF₃ | |
| (216) | —CH=CH—CH₃ | —CH=CH—CH₃ | —F | —CF₃ | |
| (217) | —CH=CH—CH₃ | —CH₂—CH=CH—CH₃ | —F | —CF₃ | |
| (218) | —CH=CH—CH₃ | —C₂H₄—CH=CH₂ | —F | —CF₃ | |
| (219) | —CH=CH—CH₃ | —C₂H₄—CH=CH—CH₃ | —F | —CF₃ | |
| (220) | —CH=CH—CH₃ | —OC₂H₅ | —F | —CF₃ | |
| (221) | —CH=CH—CH₃ | —OC₃H₇ | —F | —CF₃ | |
| (222) | —CH=CH—CH₃ | —OC₄H₉ | —F | —CF₃ | |
| (223) | —CH=CH—CH₃ | —OC₅H₁₁ | —F | —CF₃ | |
| (224) | —CH₂—CH=CH—CH₃ | —C₃H₇ | —F | —CF₃ | |
| (225) | —CH₂—CH=CH—CH₃ | —C₄H₉ | —F | —CF₃ | |
| (226) | —CH₂—CH=CH—CH₃ | —C₅H₁₁ | —F | —CF₃ | |
| (227) | —CH₂—CH=CH—CH₃ | —CH=CH₂ | —F | —CF₃ | |
| (228) | —CH₂—CH=CH—CH₃ | —CH=CH—CH₃ | —F | —CF₃ | |
| (229) | —CH₂—CH=CH—CH₃ | —CH₂—CH=CH—CH₃ | —F | —CF₃ | |
| (230) | —CH₂—CH=CH—CH₃ | —C₂H₄—CH=CH₂ | —F | —CF₃ | |
| (231) | —CH₂—CH=CH—CH₃ | —C₂H₄—CH=CH—CH₃ | —F | —CF₃ | |
| (232) | —CH₂—CH=CH—CH₃ | —OC₂H₅ | —F | —CF₃ | |
| (233) | —CH₂—CH=CH—CH₃ | —OC₃H₇ | —F | —CF₃ | |
| (234) | —CH₂—CH=CH—CH₃ | —OC₄H₉ | —F | —CF₃ | |
| (235) | —CH₂—CH=CH—CH₃ | —OC₅H₁₁ | —F | —CF₃ | |
| (236) | —C₂H₄—CH=CH₂ | —C₃H₇ | —F | —CF₃ | |
| (237) | —C₂H₄—CH=CH₂ | —C₄H₉ | —F | —CF₃ | |
| (238) | —C₂H₄—CH=CH₂ | —C₅H₁₁ | —F | —CF₃ | |
| (239) | —C₂H₄—CH=CH₂ | —CH=CH₂ | —F | —CF₃ | |
| (240) | —C₂H₄—CH=CH₂ | —CH=CH—CH₃ | —F | —CF₃ | |
| (241) | —C₂H₄—CH=CH₂ | —CH₂—CH=CH—CH₃ | —F | —CF₃ | |
| (242) | —C₂H₄—CH=CH₂ | —C₂H₄—CH=CH₂ | —F | —CF₃ | |
| (243) | —C₂H₄—CH=CH₂ | —C₂H₄—CH=CH—CH₃ | —F | —CF₃ | |
| (244) | —C₂H₄—CH=CH₂ | —OC₂H₅ | —F | —CF₃ | |
| (245) | —C₂H₄—CH=CH₂ | —OC₃H₇ | —F | —CF₃ | |
| (246) | —C₂H₄—CH=CH₂ | —OC₄H₉ | —F | —CF₃ | |
| (247) | —C₂H₄—CH=CH₂ | —OC₅H₁₁ | —F | —CF₃ | |
| (248) | —C₂H₄—CH=CH—CH₃ | —C₃H₇ | —F | —CF₃ | |
| (249) | —C₂H₄—CH=CH—CH₃ | —C₄H₉ | —F | —CF₃ | |
| (250) | —C₂H₄—CH=CH—CH₃ | —C₅H₁₁ | —F | —CF₃ | |
| (251) | —C₂H₄—CH=CH—CH₃ | —CH=CH₂ | —F | —CF₃ | |
| (252) | —C₂H₄—CH=CH—CH₃ | —CH=CH—CH₃ | —F | —CF₃ | |
| (253) | —C₂H₄—CH=CH—CH₃ | —CH₂—CH=CH—CH₃ | —F | —CF₃ | |
| (254) | —C₂H₄—CH=CH—CH₃ | —C₂H₄—CH=CH₂ | —F | —CF₃ | |
| (255) | —C₂H₄—CH=CH—CH₃ | —C₂H₄—CH=CH—CH₃ | —F | —CF₃ | |
| (256) | —C₂H₄—CH=CH—CH₃ | —OC₂H₅ | —F | —CF₃ | |
| (257) | —C₂H₄—CH=CH—CH₃ | —OC₃H₇ | —F | —CF₃ | |
| (258) | —C₂H₄—CH=CH—CH₃ | —OC₄H₉ | —F | —CF₃ | |
| (259) | —C₂H₄—CH=CH—CH₃ | —OC₅H₁₁ | —F | —CF₃ | |
| (260) | —OC₂H₅ | —C₃H₇ | —F | —CF₃ | |
| (261) | —OC₂H₅ | —C₄H₉ | —F | —CF₃ | |
| (262) | —OC₂H₅ | —C₅H₁₁ | —F | —CF₃ | $\Delta\epsilon = -17.4$; $\Delta n = 0.159$ |
| (263) | —OC₂H₅ | —OC₂H₅ | —F | —CF₃ | |
| (264) | —OC₂H₅ | —OC₃H₇ | —F | —CF₃ | |
| (265) | —OC₂H₅ | —OC₄H₉ | —F | —CF₃ | |
| (266) | —OC₂H₅ | —OC₅H₁₁ | —F | —CF₃ | |
| (267) | —OC₃H₇ | —C₃H₇ | —F | —CF₃ | |
| (268) | —OC₃H₇ | —C₄H₉ | —F | —CF₃ | |
| (269) | —OC₃H₇ | —C₅H₁₁ | —F | —CF₃ | |
| (270) | —OC₃H₇ | —OC₂H₅ | —F | —CF₃ | |
| (271) | —OC₃H₇ | —OC₃H₇ | —F | —CF₃ | |
| (272) | —OC₃H₇ | —OC₄H₉ | —F | —CF₃ | |
| (273) | —OC₃H₇ | —OC₅H₁₁ | —F | —CF₃ | |
| (274) | —OC₄H₉ | —C₃H₇ | —F | —CF₃ | |
| (275) | —OC₄H₉ | —C₄H₉ | —F | —CF₃ | |
| (276) | —OC₄H₉ | —C₅H₁₁ | —F | —CF₃ | |
| (277) | —OC₄H₉ | —OC₂H₅ | —F | —CF₃ | |
| (278) | —OC₄H₉ | —OC₃H₇ | —F | —CF₃ | |
| (279) | —OC₄H₉ | —OC₄H₉ | —F | —CF₃ | |
| (280) | —OC₄H₉ | —OC₅H₁₁ | —F | —CF₃ | |

-continued

| | R¹ | R² | L¹ | L² | |
|---|---|---|---|---|---|
| (281) | —OC₅H₁₁ | —C₃H₇ | —F | —CF₃ | |
| (282) | —OC₅H₁₁ | —C₄H₉ | —F | —CF₃ | |
| (283) | —OC₅H₁₁ | —C₅H₁₁ | —F | —CF₃ | |
| (284) | —OC₅H₁₁ | —OC₂H₅ | —F | —CF₃ | |
| (285) | —OC₅H₁₁ | —OC₃H₇ | —F | —CF₃ | |
| (286) | —OC₅H₁₁ | —OC₄H₉ | —F | —CF₃ | |
| (287) | —OC₅H₁₁ | —OC₅H₁₁ | —F | —CF₃ | |
| (288) | —C₃H₇ | —C₃H₇ | —F | —F | |
| (289) | —C₃H₇ | —C₄H₉ | —F | —F | |
| (290) | —C₃H₇ | —C₅H₁₁ | —F | —F | $\Delta\epsilon = -9.0$; $\Delta n = 0.155$ |
| (291) | —C₃H₇ | —OC₂H₅ | —F | —F | |
| (292) | —C₃H₇ | —OC₃H₇ | —F | —F | |
| (293) | —C₃H₇ | —OC₄H₉ | —F | —F | |
| (294) | —C₃H₇ | —OC₅H₁₁ | —F | —F | |
| (295) | —C₄H₉ | —C₄H₉ | —F | —F | |
| (296) | —C₄H₉ | —C₅H₁₁ | —F | —F | |
| (297) | —C₄H₉ | —OC₂H₅ | —F | —F | |
| (298) | —C₄H₉ | —OC₃H₇ | —F | —F | |
| (299) | —C₄H₉ | —OC₄H₉ | —F | —F | |
| (300) | —C₄H₉ | —OC₅H₁₁ | —F | —F | |
| (301) | —C₅H₁₁ | —C₅H₁₁ | —F | —F | |
| (302) | —C₅H₁₁ | —OC₂H₅ | —F | —F | $\Delta\epsilon = -13.7$; $\Delta n = 0.178$ |
| (303) | —C₅H₁₁ | —OC₃H₇ | —F | —F | |
| (304) | —C₅H₁₁ | —OC₄H₉ | —F | —F | |
| (305) | —C₅H₁₁ | —OC₅H₁₁ | —F | —F | |
| (306) | —CH=CH₂ | —C₃H₇ | —F | —F | |
| (307) | —CH=CH₂ | —C₄H₉ | —F | —F | |
| (308) | —CH=CH₂ | —C₅H₁₁ | —F | —F | |
| (309) | —CH=CH₂ | —CH=CH₂ | —F | —F | |
| (310) | —CH=CH₂ | —CH=CH—CH₃ | —F | —F | |
| (311) | —CH=CH₂ | —CH₂—CH=CH—CH₃ | —F | —F | |
| (312) | —CH=CH₂ | —C₂H₄—CH=CH₂ | —F | —F | |
| (313) | —CH=CH₂ | —C₂H₄—CH=CH—CH₃ | —F | —F | |
| (314) | —CH=CH₂ | —OC₂H₅ | —F | —F | |
| (315) | —CH=CH₂ | —OC₃H₇ | —F | —F | |
| (316) | —CH=CH₂ | —OC₄H₉ | —F | —F | |
| (317) | —CH=CH₂ | —OC₅H₁₁ | —F | —F | |
| (318) | —CH=CH—CH₃ | —C₃H₇ | —F | —F | |
| (319) | —CH=CH—CH₃ | —C₄H₉ | —F | —F | |
| (320) | —CH=CH—CH₃ | —C₅H₁₁ | —F | —F | |
| (321) | —CH=CH—CH₃ | —CH=CH—CH₃ | —F | —F | |
| (322) | —CH=CH—CH₃ | —CH₂—CH=CH—CH₃ | —F | —F | |
| (323) | —CH=CH—CH₃ | —C₂H₄—CH=CH₂ | —F | —F | |
| (324) | —CH=CH—CH₃ | —C₂H₄—CH=CH—CH₃ | —F | —F | |
| (325) | —CH=CH—CH₃ | —OC₂H₅ | —F | —F | |
| (326) | —CH=CH—CH₃ | —OC₃H₇ | —F | —F | |
| (327) | —CH=CH—CH₃ | —OC₄H₉ | —F | —F | |
| (328) | —CH=CH—CH₃ | —OC₅H₁₁ | —F | —F | |
| (329) | —CH₂—CH=CH—CH₃ | —C₃H₇ | —F | —F | |
| (330) | —CH₂—CH=CH—CH₃ | —C₄H₉ | —F | —F | |
| (331) | —CH₂—CH=CH—CH₃ | —C₅H₁₁ | —F | —F | |
| (332) | —CH₂—CH=CH—CH₃ | —CH₂—CH=CH—CH₃ | —F | —F | |
| (333) | —CH₂—CH=CH—CH₃ | —C₂H₄—CH=CH₂ | —F | —F | |
| (334) | —CH₂—CH=CH—CH₃ | —C₂H₄—CH=CH—CH₃ | —F | —F | |
| (335) | —CH₂—CH=CH—CH₃ | —OC₂H₅ | —F | —F | |
| (336) | —CH₂—CH=CH—CH₃ | —OC₃H₇ | —F | —F | |
| (337) | —CH₂—CH=CH—CH₃ | —OC₄H₉ | —F | —F | |
| (338) | —CH₂—CH=CH—CH₃ | —OC₅H₁₁ | —F | —F | |
| (339) | —C₂H₄—CH=CH₂ | —C₃H₇ | —F | —F | |
| (340) | —C₂H₄—CH=CH₂ | —C₄H₉ | —F | —F | |
| (341) | —C₂H₄—CH=CH₂ | —C₅H₁₁ | —F | —F | |
| (342) | —C₂H₄—CH=CH₂ | —C₂H₄—CH=CH₂ | —F | —F | |
| (343) | —C₂H₄—CH=CH₂ | —C₂H₄—CH=CH—CH₃ | —F | —F | |
| (344) | —C₂H₄—CH=CH₂ | —OC₂H₅ | —F | —F | |
| (345) | —C₂H₄—CH=CH₂ | —OC₃H₇ | —F | —F | |
| (346) | —C₂H₄—CH=CH₂ | —OC₄H₉ | —F | —F | |
| (347) | —C₂H₄—CH=CH₂ | —OC₅H₁₁ | —F | —F | |
| (348) | —C₂H₄—CH=CH—CH₃ | —C₃H₇ | —F | —F | |
| (349) | —C₂H₄—CH=CH—CH₃ | —C₄H₉ | —F | —F | |
| (350) | —C₂H₄—CH=CH—CH₃ | —C₅H₁₁ | —F | —F | |
| (351) | —C₂H₄—CH=CH—CH₃ | —C₂H₄—CH=CH—CH₃ | —F | —F | |
| (352) | —C₂H₄—CH=CH—CH₃ | —OC₂H₅ | —F | —F | |
| (353) | —C₂H₄—CH=CH—CH₃ | —OC₃H₇ | —F | —F | |
| (354) | —C₂H₄—CH=CH—CH₃ | —OC₄H₉ | —F | —F | |
| (355) | —C₂H₄—CH=CH—CH₃ | —OC₅H₁₁ | —F | —F | |

-continued

| | R¹ | R² | L¹ | L² |
|---|---|---|---|---|
| (356) | —OC$_2$H$_5$ | —OC$_2$H$_5$ | —F | —F |
| (357) | —OC$_2$H$_5$ | —OC$_3$H$_7$ | —F | —F |
| (358) | —OC$_2$H$_5$ | —OC$_4$H$_9$ | —F | —F |
| (359) | —OC$_2$H$_5$ | —OC$_5$H$_{11}$ | —F | —F |
| (360) | —OC$_3$H$_7$ | —OC$_3$H$_7$ | —F | —F |
| (361) | —OC$_3$H$_7$ | —OC$_4$H$_9$ | —F | —F |
| (362) | —OC$_3$H$_7$ | —OC$_5$H$_{11}$ | —F | —F |
| (363) | —OC$_4$H$_9$ | —OC$_4$H$_9$ | —F | —F |
| (364) | —OC$_4$H$_9$ | —OC$_5$H$_{11}$ | —F | —F |
| (365) | —OC$_5$H$_{11}$ | —OC$_5$H$_{11}$ | —F | —F |
| (366) | —C$_3$H$_7$ | —C$_3$H$_7$ | —CF$_3$ | —CF$_3$ |
| (367) | —C$_3$H$_7$ | —C$_4$H$_9$ | —CF$_3$ | —CF$_3$ |
| (368) | —C$_3$H$_7$ | —C$_5$H$_{11}$ | —CF$_3$ | —CF$_3$ |
| (369) | —C$_3$H$_7$ | —OC$_2$H$_5$ | —CF$_3$ | —CF$_3$ |
| (370) | —C$_3$H$_7$ | —OC$_3$H$_7$ | —CF$_3$ | —CF$_3$ |
| (371) | —C$_3$H$_7$ | —OC$_4$H$_9$ | —CF$_3$ | —CF$_3$ |
| (372) | —C$_3$H$_7$ | —OC$_5$H$_{11}$ | —CF$_3$ | —CF$_3$ |
| (373) | —C$_4$H$_9$ | —C$_4$H$_9$ | —CF$_3$ | —CF$_3$ |
| (374) | —C$_4$H$_9$ | —C$_5$H$_{11}$ | —CF$_3$ | —CF$_3$ |
| (375) | —C$_4$H$_9$ | —OC$_2$H$_5$ | —CF$_3$ | —CF$_3$ |
| (376) | —C$_4$H$_9$ | —OC$_3$H$_7$ | —CF$_3$ | —CF$_3$ |
| (377) | —C$_4$H$_9$ | —OC$_4$H$_9$ | —CF$_3$ | —CF$_3$ |
| (378) | —C$_4$H$_9$ | —OC$_5$H$_{11}$ | —CF$_3$ | —CF$_3$ |
| (379) | —C$_5$H$_{11}$ | —C$_5$H$_{11}$ | —CF$_3$ | —CF$_3$ |
| (380) | —C$_5$H$_{11}$ | —OC$_2$H$_5$ | —CF$_3$ | —CF$_3$ |
| (381) | —C$_5$H$_{11}$ | —OC$_3$H$_7$ | —CF$_3$ | —CF$_3$ |
| (382) | —C$_5$H$_{11}$ | —OC$_4$H$_9$ | —CF$_3$ | —CF$_3$ |
| (383) | —C$_5$H$_{11}$ | —OC$_5$H$_{11}$ | —CF$_3$ | —CF$_3$ |
| (384) | —OC$_2$H$_5$ | —OC$_2$H$_5$ | —CF$_3$ | —CF$_3$ |
| (385) | —OC$_2$H$_5$ | —OC$_3$H$_7$ | —CF$_3$ | —CF$_3$ |
| (386) | —OC$_2$H$_5$ | —OC$_4$H$_9$ | —CF$_3$ | —CF$_3$ |
| (387) | —OC$_2$H$_5$ | —OC$_5$H$_{11}$ | —CF$_3$ | —CF$_3$ |
| (388) | —OC$_3$H$_7$ | —OC$_3$H$_7$ | —CF$_3$ | —CF$_3$ |
| (389) | —OC$_3$H$_7$ | —OC$_4$H$_9$ | —CF$_3$ | —CF$_3$ |
| (390) | —OC$_3$H$_7$ | —OC$_5$H$_{11}$ | —CF$_3$ | —CF$_3$ |
| (391) | —OC$_4$H$_9$ | —OC$_4$H$_9$ | —CF$_3$ | —CF$_3$ |
| (392) | —OC$_4$H$_9$ | —OC$_5$H$_{11}$ | —CF$_3$ | —CF$_3$ |
| (393) | —OC$_5$H$_{11}$ | —OC$_5$H$_{11}$ | —CF$_3$ | —CF$_3$ |

Fluorene compounds of the following formulae

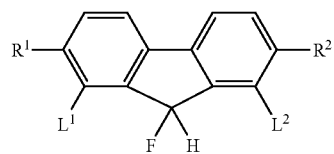

40

45 are obtained analogously to Example 2:

| | R¹ | R² | L¹ | L² |
|---|---|---|---|---|
| (400) | —C$_3$H$_7$ | —C$_3$H$_7$ | —H | —F |
| (401) | —C$_3$H$_7$ | —C$_4$H$_9$ | —H | —F |
| (402) | —C$_3$H$_7$ | —C$_5$H$_{11}$ | —H | —F |
| (403) | —C$_3$H$_7$ | —OC$_2$H$_5$ | —H | —F |
| (404) | —C$_3$H$_7$ | —OC$_3$H$_7$ | —H | —F |
| (405) | —C$_3$H$_7$ | —OC$_4$H$_9$ | —H | —F |
| (406) | —C$_3$H$_7$ | —OC$_5$H$_{11}$ | —H | —F |
| (407) | —C$_4$H$_9$ | —C$_3$H$_7$ | —H | —F |
| (408) | —C$_4$H$_9$ | —C$_4$H$_9$ | —H | —F |
| (409) | —C$_4$H$_9$ | —C$_5$H$_{11}$ | —H | —F |
| (410) | —C$_4$H$_9$ | —OC$_2$H$_5$ | —H | —F |
| (411) | —C$_4$H$_9$ | —OC$_3$H$_7$ | —H | —F |
| (412) | —C$_4$H$_9$ | —OC$_4$H$_9$ | —H | —F |
| (413) | —C$_4$H$_9$ | —OC$_5$H$_{11}$ | —H | —F |
| (414) | —C$_5$H$_{11}$ | —C$_3$H$_7$ | —H | —F |
| (415) | —C$_5$H$_{11}$ | —C$_4$H$_9$ | —H | —F |

-continued

| | R¹ | R² | L¹ | L² |
|---|---|---|---|---|
| (416) | —C₅H₁₁ | —C₅H₁₁ | —H | —F |
| (417) | —C₅H₁₁ | —OC₂H₅ | —H | —F |
| (418) | —C₅H₁₁ | —OC₃H₇ | —H | —F |
| (419) | —C₅H₁₁ | —OC₄H₉ | —H | —F |
| (420) | —C₅H₁₁ | —OC₅H₁₁ | —H | —F |
| (421) | —CH=CH₂ | —C₃H₇ | —H | —F |
| (422) | —CH=CH₂ | —C₄H₉ | —H | —F |
| (423) | —CH=CH₂ | —C₅H₁₁ | —H | —F |
| (424) | —CH=CH₂ | —CH=CH₂ | —H | —F |
| (425) | —CH=CH₂ | —CH=CH—CH₃ | —H | —F |
| (426) | —CH=CH₂ | —CH₂—CH=CH—CH₃ | —H | —F |
| (427) | —CH=CH₂ | —C₂H₄—CH=CH₂ | —H | —F |
| (428) | —CH=CH₂ | —C₂H₄—CH=CH—CH3 | —H | —F |
| (429) | —CH=CH₂ | —OC₂H₅ | —H | —F |
| (430) | —CH=CH₂ | —OC₃H₇ | —H | —F |
| (431) | —CH=CH₂ | —OC₄H₉ | —H | —F |
| (432) | —CH=CH₂ | —OC₅H₁₁ | —H | —F |
| (433) | —CH=CH—CH₃ | —C₃H₇ | —H | —F |
| (434) | —CH=CH—CH₃ | —C₄H₉ | —H | —F |
| (435) | —CH=CH—CH₃ | —C₅H₁₁ | —H | —F |
| (436) | —CH=CH—CH₃ | —CH=CH₂ | —H | —F |
| (437) | —CH=CH—CH₃ | —CH=CH—CH₃ | —H | —F |
| (438) | —CH=CH—CH₃ | —CH₂—CH=CH—CH₃ | —H | —F |
| (439) | —CH=CH—CH₃ | —C₂H₄—CH=CH₂ | —H | —F |
| (440) | —CH=CH—CH₃ | —C₂H₄—CH=CH—CH₃ | —H | —F |
| (441) | —CH=CH—CH₃ | —OC₂H₅ | —H | —F |
| (442) | —CH=CH—CH₃ | —OC₃H₇ | —H | —F |
| (443) | —CH=CH—CH₃ | —OC₄H₉ | —H | —F |
| (444) | —CH=CH—CH₃ | —OC₅H₁₁ | —H | —F |
| (445) | —CH₂—CH=CH—CH₃ | —C₃H₇ | —H | —F |
| (446) | —CH₂—CH=CH—CH₃ | —C₄H₉ | —H | —F |
| (447) | —CH₂—CH=CH—CH₃ | —C₅H₁₁ | —H | —F |
| (448) | —CH₂—CH=CH—CH₃ | —CH=CH₂ | —H | —F |
| (449) | —CH₂—CH=CH—CH₃ | —CH=CH—CH₃ | —H | —F |
| (450) | —CH₂—CH=CH—CH₃ | —CH₂—CH=CH—CH₃ | —H | —F |
| (451) | —CH₂—CH=CH—CH₃ | —C₂H₄—CH=CH₂ | —H | —F |
| (452) | —CH₂—CH=CH—CH₃ | —C₂H₄—CH=CH—CH₃ | —H | —F |
| (453) | —CH₂—CH=CH—CH₃ | —OC₂H₅ | —H | —F |
| (454) | —CH₂—CH=CH—CH₃ | —OC₃H₇ | —H | —F |
| (455) | —CH₂—CH=CH—CH₃ | —OC₄H₉ | —H | —F |
| (456) | —CH₂—CH=CH—CH₃ | —OC₅H₁₁ | —H | —F |
| (457) | —C₂H₄—CH=CH₂ | —C₃H₇ | —H | —F |
| (458) | —C₂H₄—CH=CH₂ | —C₄H₉ | —H | —F |
| (459) | —C₂H₄—CH=CH₂ | —C₅H₁₁ | —H | —F |
| (460) | —C₂H₄—CH=CH₂ | —CH=CH₂ | —H | —F |
| (461) | —C₂H₄—CH=CH₂ | —CH=CH—CH₃ | —H | —F |
| (462) | —C₂H₄—CH=CH₂ | —CH₂—CH=CH—CH₃ | —H | —F |
| (463) | —C₂H₄—CH=CH₂ | —C₂H₄—CH=CH₂ | —H | —F |
| (464) | —C₂H₄—CH=CH₂ | —C₂H₄—CH=CH—CH₃ | —H | —F |
| (465) | —C₂H₄—CH=CH₂ | —OC₂H₅ | —H | —F |
| (466) | —C₂H₄—CH=CH₂ | —OC₃H₇ | —H | —F |
| (467) | —C₂H₄—CH=CH₂ | —OC₄H₉ | —H | —F |
| (468) | —C₂H₄—CH=CH₂ | —OC₅H₁₁ | —H | —F |
| (469) | —C₂H₄—CH=CH—CH₃ | —C₃H₇ | —H | —F |
| (470) | —C₂H₄—CH=CH—CH₃ | —C₄H₉ | —H | —F |
| (471) | —C₂H₄—CH=CH—CH₃ | —C₅H₁₁ | —H | —F |
| (472) | —C₂H₄—CH=CH—CH₃ | —CH=CH₂ | —H | —F |
| (473) | —C₂H₄—CH=CH—CH₃ | —CH=CH—CH₃ | —H | —F |
| (474) | —C₂H₄—CH=CH—CH₃ | —CH₂—CH=CH—CH₃ | —H | —F |
| (475) | —C₂H₄—CH=CH—CH₃ | —C₂H₄—CH=CH₂ | —H | —F |
| (476) | —C₂H₄—CH=CH—CH₃ | —C₂H₄—CH=CH—CH₃ | —H | —F |
| (477) | —C₂H₄—CH=CH—CH₃ | —OC₂H₅ | —H | —F |
| (478) | —C₂H₄—CH=CH—CH₃ | —OC₃H₇ | —H | —F |
| (479) | —C₂H₄—CH=CH—CH₃ | —OC₄H₉ | —H | —F |
| (480) | —C₂H₄—CH=CH—CH₃ | —OC₅H₁₁ | —H | —F |
| (481) | —OC₂H₅ | —C₃H₇ | —H | —F |
| (482) | —OC₂H₅ | —C₄H₉ | —H | —F |
| (483) | —OC₂H₅ | —C₅H₁₁ | —H | —F |
| (484) | —OC₂H₅ | —OC₂H₅ | —H | —F |
| (485) | —OC₂H₅ | —OC₃H₇ | —H | —F |
| (486) | —OC₂H₅ | —OC₄H₉ | —H | —F |
| (487) | —OC₂H₅ | —OC₅H₁₁ | —H | —F |
| (488) | —OC₃H₇ | —C₃H₇ | —H | —F |
| (489) | —OC₃H₇ | —C₄H₉ | —H | —F |
| (490) | —OC₃H₇ | —C₅H₁₁ | —H | —F |
| (491) | —OC₃H₇ | —OC₂H₅ | —H | —F |
| (492) | —OC₃H₇ | —OC₃H₇ | —H | —F |

-continued

| | R¹ | R² | L¹ | L² |
|---|---|---|---|---|
| (493) | —OC₃H₇ | —OC₄H₉ | —H | —F |
| (494) | —OC₃H₇ | —OC₅H₁₁ | —H | —F |
| (495) | —OC₄H₉ | —C₃H₇ | —H | —F |
| (496) | —OC₄H₉ | —C₄H₉ | —H | —F |
| (497) | —OC₄H₉ | —C₅H₁₁ | —H | —F |
| (498) | —OC₄H₉ | —OC₂H₅ | —H | —F |
| (499) | —OC₄H₉ | —OC₃H₇ | —H | —F |
| (500) | —OC₄H₉ | —OC₄H₉ | —H | —F |
| (501) | —OC₄H₉ | —OC₅H₁₁ | —H | —F |
| (502) | —OC₅H₁₁ | —C₃H₇ | —H | —F |
| (503) | —OC₅H₁₁ | —C₄H₉ | —H | —F |
| (504) | —OC₅H₁₁ | —C₅H₁₁ | —H | —F |
| (505) | —OC₅H₁₁ | —OC₂H₅ | —H | —F |
| (506) | —OC₅H₁₁ | —OC₃H₇ | —H | —F |
| (507) | —OC₅H₁₁ | —OC₄H₉ | —H | —F |
| (508) | —OC₅H₁₁ | —OC₅H₁₁ | —H | —F |
| (509) | —C₃H₇ | —C₃H₇ | —H | —CF₃ |
| (510) | —C₃H₇ | —C₄H₉ | —H | —CF₃ |
| (511) | —C₃H₇ | —C₅H₁₁ | —H | —CF₃ |
| (512) | —C₃H₇ | —OC₂H₅ | —H | —CF₃ |
| (513) | —C₃H₇ | —OC₃H₇ | —H | —CF₃ |
| (514) | —C₃H₇ | —OC₄H₉ | —H | —CF₃ |
| (515) | —C₃H₇ | —OC₅H₁₁ | —H | —CF₃ |
| (516) | —C₄H₉ | —C₃H₇ | —H | —CF₃ |
| (517) | —C₄H₉ | —C₄H₉ | —H | —CF₃ |
| (518) | —C₄H₉ | —C₅H₁₁ | —H | —CF₃ |
| (519) | —C₄H₉ | —OC₂H₅ | —H | —CF₃ |
| (520) | —C₄H₉ | —OC₃H₇ | —H | —CF₃ |
| (521) | —C₄H₉ | —OC₄H₉ | —H | —CF₃ |
| (522) | —C₄H₉ | —OC₅H₁₁ | —H | —CF₃ |
| (523) | —C₅H₁₁ | —C₃H₇ | —H | —CF₃ |
| (524) | —C₅H₁₁ | —C₄H₉ | —H | —CF₃ |
| (525) | —C₅H₁₁ | —C₅H₁₁ | —H | —CF₃ |
| (526) | —C₅H₁₁ | —OC₂H₅ | —H | —CF₃ |
| (527) | —C₅H₁₁ | —OC₃H₇ | —H | —CF₃ |
| (528) | —C₅H₁₁ | —OC₄H₉ | —H | —CF₃ |
| (529) | —C₅H₁₁ | —OC₅H₁₁ | —H | —CF₃ |
| (530) | —OC₂H₅ | —C₃H₇ | —H | —CF₃ |
| (531) | —OC₂H₅ | —C₄H₉ | —H | —CF₃ |
| (532) | —OC₂H₅ | —C₅H₁₁ | —H | —CF₃ |
| (533) | —OC₂H₅ | —OC₂H₅ | —H | —CF₃ |
| (534) | —OC₂H₅ | —OC₃H₇ | —H | —CF₃ |
| (535) | —OC₂H₅ | —OC₄H₉ | —H | —CF₃ |
| (536) | —OC₂H₅ | —OC₅H₁₁ | —H | —CF₃ |
| (537) | —OC₃H₇ | —C₃H₇ | —H | —CF₃ |
| (538) | —OC₃H₇ | —C₄H₉ | —H | —CF₃ |
| (539) | —OC₃H₇ | —C₅H₁₁ | —H | —CF₃ |
| (540) | —OC₃H₇ | —OC₂H₅ | —H | —CF₃ |
| (541) | —OC₃H₇ | —OC₃H₇ | —H | —CF₃ |
| (542) | —OC₃H₇ | —OC₄H₉ | —H | —CF₃ |
| (543) | —OC₃H₇ | —OC₅H₁₁ | —H | —CF₃ |
| (544) | —OC₄H₉ | —C₃H₇ | —H | —CF₃ |
| (545) | —OC₄H₉ | —C₄H₉ | —H | —CF₃ |
| (546) | —OC₄H₉ | —C₅H₁₁ | —H | —CF₃ |
| (547) | —OC₄H₉ | —OC₂H₅ | —H | —CF₃ |
| (548) | —OC₄H₉ | —OC₃H₇ | —H | —CF₃ |
| (549) | —OC₄H₉ | —OC₄H₉ | —H | —CF₃ |
| (550) | —OC₄H₉ | —OC₅H₁₁ | —H | —CF₃ |
| (551) | —OC₅H₁₁ | —C₃H₇ | —H | —CF₃ |
| (552) | —OC₅H₁₁ | —C₄H₉ | —H | —CF₃ |
| (553) | —OC₅H₁₁ | —C₅H₁₁ | —H | —CF₃ |
| (554) | —OC₅H₁₁ | —OC₂H₅ | —H | —CF₃ |
| (555) | —OC₅H₁₁ | —OC₃H₇ | —H | —CF₃ |
| (556) | —OC₅H₁₁ | —OC₄H₉ | —H | —CF₃ |
| (557) | —OC₅H₁₁ | —OC₅H₁₁ | —H | —CF₃ |
| (558) | —C₃H₇ | —C₃H₇ | —F | —CF₃ |
| (559) | —C₃H₇ | —C₄H₉ | —F | —CF₃ |
| (560) | —C₃H₇ | —C₅H₁₁ | —F | —CF₃ |
| (561) | —C₃H₇ | —OC₂H₅ | —F | —CF₃ |
| (562) | —C₃H₇ | —OC₃H₇ | —F | —CF₃ |
| (563) | —C₃H₇ | —OC₄H₉ | —F | —CF₃ |
| (564) | —C₃H₇ | —OC₅H₁₁ | —F | —CF₃ |
| (565) | —C₄H₉ | —C₃H₇ | —F | —CF₃ |
| (566) | —C₄H₉ | —C₄H₉ | —F | —CF₃ |
| (567) | —C₄H₉ | —C₅H₁₁ | —F | —CF₃ |
| (568) | —C₄H₉ | —OC₂H₅ | —F | —CF₃ |
| (569) | —C₄H₉ | —OC₃H₇ | —F | —CF₃ |

-continued

| | R¹ | R² | L¹ | L² |
|---|---|---|---|---|
| (570) | —C₄H₉ | —OC₄H₉ | —F | —CF₃ |
| (571) | —C₄H₉ | —OC₅H₁₁ | —F | —CF₃ |
| (572) | —C₅H₁₁ | —C₃H₇ | —F | —CF₃ |
| (573) | —C₅H₁₁ | —C₄H₉ | —F | —CF₃ |
| (574) | —C₅H₁₁ | —C₅H₁₁ | —F | —CF₃ |
| (575) | —C₅H₁₁ | —OC₂H₅ | —F | —CF₃ |
| (576) | —C₅H₁₁ | —OC₃H₇ | —F | —CF₃ |
| (577) | —C₅H₁₁ | —OC₄H₉ | —F | —CF₃ |
| (578) | —C₅H₁₁ | —OC₅H₁₁ | —F | —CF₃ |
| (579) | —CH=CH₂ | —C₃H₇ | —F | —CF₃ |
| (580) | —CH=CH₂ | —C₄H₉ | —F | —CF₃ |
| (581) | —CH=CH₂ | —C₅H₁₁ | —F | —CF₃ |
| (582) | —CH=CH₂ | —CH=CH₂ | —F | —CF₃ |
| (583) | —CH=CH₂ | —CH=CH—CH₃ | —F | —CF₃ |
| (584) | —CH=CH₂ | —CH₂—CH=CH—CH₃ | —F | —CF₃ |
| (585) | —CH=CH₂ | —C₂H₄—CH=CH₂ | —F | —CF₃ |
| (586) | —CH=CH₂ | —C₂H₄—CH=CH—CH₃ | —F | —CF₃ |
| (587) | —CH=CH₂ | —OC₂H₅ | —F | —CF₃ |
| (588) | —CH=CH₂ | —OC₃H₇ | —F | —CF₃ |
| (589) | —CH=CH₂ | —OC₄H₉ | —F | —CF₃ |
| (590) | —CH=CH₂ | —OC₅H₁₁ | —F | —CF₃ |
| (591) | —CH=CH—CH₃ | —C₃H₇ | —F | —CF₃ |
| (592) | —CH=CH—CH₃ | —C₄H₉ | —F | —CF₃ |
| (593) | —CH=CH—CH₃ | —C₅H₁₁ | —F | —CF₃ |
| (594) | —CH=CH—CH₃ | —CH=CH₂ | —F | —CF₃ |
| (595) | —CH=CH—CH₃ | —CH=CH—CH₃ | —F | —CF₃ |
| (596) | —CH=CH—CH₃ | —CH₂—CH=CH—CH₃ | —F | —CF₃ |
| (597) | —CH=CH—CH₃ | —C₂H₄—CH=CH₂ | —F | —CF₃ |
| (598) | —CH=CH—CH₃ | —C₂H₄—CH=CH—CH₃ | —F | —CF₃ |
| (599) | —CH=CH—CH₃ | —OC₂H₅ | —F | —CF₃ |
| (600) | —CH=CH—CH₃ | —OC₃H₇ | —F | —CF₃ |
| (601) | —CH=CH—CH₃ | —OC₄H₉ | —F | —CF₃ |
| (602) | —CH=CH—CH₃ | —OC₅H₁₁ | —F | —CF₃ |
| (603) | —CH₂—CH=CH—CH₃ | —C₃H₇ | —F | —CF₃ |
| (604) | —CH₂—CH=CH—CH₃ | —C₄H₉ | —F | —CF₃ |
| (605) | —CH₂—CH=CH—CH₃ | —C₅H₁₁ | —F | —CF₃ |
| (606) | —CH₂—CH=CH—CH₃ | —CH=CH₂ | —F | —CF₃ |
| (607) | —CH₂—CH=CH—CH₃ | —CH=CH—CH₃ | —F | —CF₃ |
| (608) | —CH₂—CH=CH—CH₃ | —CH₂—CH=CH—CH₃ | —F | —CF₃ |
| (609) | —CH₂—CH=CH—CH₃ | —C₂H₄—CH=CH₂ | —F | —CF₃ |
| (610) | —CH₂—CH=CH—CH₃ | —C₂H₄—CH=CH—CH₃ | —F | —CF₃ |
| (611) | —CH₂—CH=CH—CH₃ | —OC₂H₅ | —F | —CF₃ |
| (612) | —CH₂—CH=CH—CH₃ | —OC₃H₇ | —F | —CF₃ |
| (613) | —CH₂—CH=CH—CH₃ | —OC₄H₉ | —F | —CF₃ |
| (614) | —CH₂—CH=CH—CH₃ | —OC₅H₁₁ | —F | —CF₃ |
| (615) | —C₂H₄—CH=CH₂ | —C₃H₇ | —F | —CF₃ |
| (616) | —C₂H₄—CH=CH₂ | —C₄H₉ | —F | —CF₃ |
| (617) | —C₂H₄—CH=CH₂ | —C₅H₁₁ | —F | —CF₃ |
| (618) | —C₂H₄—CH=CH₂ | —CH=CH₂ | —F | —CF₃ |
| (619) | —C₂H₄—CH=CH₂ | —CH=CH—CH₃ | —F | —CF₃ |
| (620) | —C₂H₄—CH=CH₂ | —CH₂—CH=CH—CH₃ | —F | —CF₃ |
| (621) | —C₂H₄—CH=CH₂ | —C₂H₄—CH=CH₂ | —F | —CF₃ |
| (622) | —C₂H₄—CH=CH₂ | —C₂H₄—CH=CH—CH₃ | —F | —CF₃ |
| (623) | —C₂H₄—CH=CH₂ | —OC₂H₅ | —F | —CF₃ |
| (624) | —C₂H₄—CH=CH₂ | —OC₃H₇ | —F | —CF₃ |
| (625) | —C₂H₄—CH=CH₂ | —OC₄H₉ | —F | —CF₃ |
| (626) | —C₂H₄—CH=CH₂ | —OC₅H₁₁ | —F | —CF₃ |
| (627) | —C₂H₄—CH=CH—CH₃ | —C₃H₇ | —F | —CF₃ |
| (628) | —C₂H₄—CH=CH—CH₃ | —C₄H₉ | —F | —CF₃ |
| (629) | —C₂H₄—CH=CH—CH₃ | —C₅H₁₁ | —F | —CF₃ |
| (630) | —C₂H₄—CH=CH—CH₃ | —CH=CH₂ | —F | —CF₃ |
| (631) | —C₂H₄—CH=CH—CH₃ | —CH=CH—CH₃ | —F | —CF₃ |
| (632) | —C₂H₄—CH=CH—CH₃ | —CH₂—CH=CH—CH₃ | —F | —CF₃ |
| (633) | —C₂H₄—CH=CH—CH₃ | —C₂H₄—CH=CH₂ | —F | —CF₃ |
| (634) | —C₂H₄—CH=CH—CH₃ | —C₂H₄—CH=CH—CH₃ | —F | —CF₃ |
| (635) | —C₂H₄—CH=CH—CH₃ | —OC₂H₅ | —F | —CF₃ |
| (636) | —C₂H₄—CH=CH—CH₃ | —OC₃H₇ | —F | —CF₃ |
| (637) | —C₂H₄—CH=CH—CH₃ | —OC₄H₉ | —F | —CF₃ |
| (638) | —C₂H₄—CH=CH—CH₃ | —OC₅H₁₁ | —F | —CF₃ |
| (639) | —OC₂H₅ | —C₃H₇ | —F | —CF₃ |
| (640) | —OC₂H₅ | —C₄H₉ | —F | —CF₃ |
| (641) | —OC₂H₅ | —C₅H₁₁ | —F | —CF₃ |
| (642) | —OC₂H₅ | —OC₂H₅ | —F | —CF₃ |
| (643) | —OC₂H₅ | —OC₃H₇ | —F | —CF₃ |
| (644) | —OC₂H₅ | —OC₄H₉ | —F | —CF₃ |
| (645) | —OC₂H₅ | —OC₅H₁₁ | —F | —CF₃ |
| (646) | —OC₃H₇ | —C₃H₇ | —F | —CF₃ |

-continued

| | R¹ | R² | L¹ | L² |
|---|---|---|---|---|
| (647) | —OC₃H₇ | —C₄H₉ | —F | —CF₃ |
| (648) | —OC₃H₇ | —C₅H₁₁ | —F | —CF₃ |
| (649) | —OC₃H₇ | —OC₂H₅ | —F | —CF₃ |
| (650) | —OC₃H₇ | —OC₃H₇ | —F | —CF₃ |
| (651) | —OC₃H₇ | —OC₄H₉ | —F | —CF₃ |
| (652) | —OC₃H₇ | —OC₅H₁₁ | —F | —CF₃ |
| (653) | —OC₄H₉ | —C₃H₇ | —F | —CF₃ |
| (654) | —OC₄H₉ | —C₄H₉ | —F | —CF₃ |
| (655) | —OC₄H₉ | —C₅H₁₁ | —F | —CF₃ |
| (656) | —OC₄H₉ | —OC₂H₅ | —F | —CF₃ |
| (657) | —OC₄H₉ | —OC₃H₇ | —F | —CF₃ |
| (658) | —OC₄H₉ | —OC₄H₉ | —F | —CF₃ |
| (659) | —OC₄H₉ | —OC₅H₁₁ | —F | —CF₃ |
| (660) | —OC₅H₁₁ | —C₃H₇ | —F | —CF₃ |
| (661) | —OC₅H₁₁ | —C₄H₉ | —F | —CF₃ |
| (662) | —OC₅H₁₁ | —C₅H₁₁ | —F | —CF₃ |
| (663) | —OC₅H₁₁ | —OC₂H₅ | —F | —CF₃ |
| (664) | —OC₅H₁₁ | —OC₃H₇ | —F | —CF₃ |
| (665) | —OC₅H₁₁ | —OC₄H₉ | —F | —CF₃ |
| (666) | —OC₅H₁₁ | —OC₅H₁₁ | —F | —CF₃ |
| (667) | —C₃H₇ | —C₃H₇ | —F | —F |
| (668) | —C₃H₇ | —C₄H₉ | —F | —F |
| (669) | —C₃H₇ | —C₅H₁₁ | —F | —F |
| (670) | —C₃H₇ | —OC₂H₅ | —F | —F |
| (671) | —C₃H₇ | —OC₃H₇ | —F | —F |
| (672) | —C₃H₇ | —OC₄H₉ | —F | —F |
| (673) | —C₃H₇ | —OC₅H₁₁ | —F | —F |
| (674) | —C₄H₉ | —C₄H₉ | —F | —F |
| (675) | —C₄H₉ | —C₅H₁₁ | —F | —F |
| (676) | —C₄H₉ | —OC₂H₅ | —F | —F |
| (677) | —C₄H₉ | —OC₃H₇ | —F | —F |
| (678) | —C₄H₉ | —OC₄H₉ | —F | —F |
| (679) | —C₄H₉ | —OC₅H₁₁ | —F | —F |
| (680) | —C₅H₁₁ | —C₅H₁₁ | —F | —F |
| (681) | —C₅H₁₁ | —OC₂H₅ | —F | —F |
| (682) | —C₅H₁₁ | —OC₃H₇ | —F | —F |
| (683) | —C₅H₁₁ | —OC₄H₉ | —F | —F |
| (684) | —C₅H₁₁ | —OC₅H₁₁ | —F | —F |
| (685) | —CH=CH₂ | —C₃H₇ | —F | —F |
| (686) | —CH=CH₂ | —C₄H₉ | —F | —F |
| (687) | —CH=CH₂ | —C₅H₁₁ | —F | —F |
| (688) | —CH=CH₂ | —CH=CH₂ | —F | —F |
| (689) | —CH=CH₂ | —CH=CH—CH₃ | —F | —F |
| (690) | —CH=CH₂ | —CH₂—CH=CH—CH₃ | —F | —F |
| (691) | —CH=CH₂ | —C₂H₄—CH=CH₂ | —F | —F |
| (692) | —CH=CH₂ | —C₂H₄—CH=CH—CH₃ | —F | —F |
| (693) | —CH=CH₂ | —OC₂H₅ | —F | —F |
| (694) | —CH=CH₂ | —OC₃H₇ | —F | —F |
| (695) | —CH=CH₂ | —OC₄H₉ | —F | —F |
| (696) | —CH=CH₂ | —OC₅H₁₁ | —F | —F |
| (697) | —CH=CH—CH₃ | —C₃H₇ | —F | —F |
| (698) | —CH=CH—CH₃ | —C₄H₉ | —F | —F |
| (699) | —CH=CH—CH₃ | —C₅H₁₁ | —F | —F |
| (700) | —CH=CH—CH₃ | —CH=CH—CH₃ | —F | —F |
| (701) | —CH=CH—CH₃ | —CH₂—CH=CH—CH₃ | —F | —F |
| (702) | —CH=CH—CH₃ | —C₂H₄—CH=CH₂ | —F | —F |
| (703) | —CH=CH—CH₃ | —C₂H₄—CH=CH—CH₃ | —F | —F |
| (704) | —CH=CH—CH₃ | —OC₂H₅ | —F | —F |
| (705) | —CH=CH—CH₃ | —OC₃H₇ | —F | —F |
| (706) | —CH=CH—CH₃ | —OC₄H₉ | —F | —F |
| (707) | —CH=CH—CH₃ | —OC₅H₁₁ | —F | —F |
| (708) | —CH₂—CH=CH—CH₃ | —C₃H₇ | —F | —F |
| (709) | —CH₂—CH=CH—CH₃ | —C₄H₉ | —F | —F |
| (710) | —CH₂—CH=CH—CH₃ | —C₅H₁₁ | —F | —F |
| (711) | —CH₂—CH=CH—CH₃ | —CH₂—CH=CH—CH₃ | —F | —F |
| (712) | —CH₂—CH=CH—CH₃ | —C₂H₄—CH=CH₂ | —F | —F |
| (713) | —CH₂—CH=CH—CH₃ | —C₂H₄—CH=CH—CH₃ | —F | —F |
| (714) | —CH₂—CH=CH—CH₃ | —OC₂H₅ | —F | —F |
| (715) | —CH₂—CH=CH—CH₃ | —OC₃H₇ | —F | —F |
| (716) | —CH₂—CH=CH—CH₃ | —OC₄H₉ | —F | —F |
| (717) | —CH₂—CH=CH—CH₃ | —OC₅H₁₁ | —F | —F |
| (718) | —C₂H₄—CH=CH₂ | —C₃H₇ | —F | —F |
| (719) | —C₂H₄—CH=CH₂ | —C₄H₉ | —F | —F |
| (720) | —C₂H₄—CH=CH₂ | —C₅H₁₁ | —F | —F |
| (721) | —C₂H₄—CH=CH₂ | —C₂H₄—CH=CH₂ | —F | —F |
| (722) | —C₂H₄—CH=CH₂ | —C₂H₄—CH=CH—CH₃ | —F | —F |
| (723) | —C₂H₄—CH=CH₂ | —OC₂H₅ | —F | —F |

-continued

| | R¹ | R² | L¹ | L² |
|---|---|---|---|---|
| (724) | —C₂H₄—CH=CH₂ | —OC₃H₇ | —F | —F |
| (725) | —C₂H₄—CH=CH₂ | —OC₄H₉ | —F | —F |
| (726) | —C₂H₄—CH=CH₂ | —OC₅H₁₁ | —F | —F |
| (727) | —C₂H₄—CH=CH—CH₃ | —C₃H₇ | —F | —F |
| (728) | —C₂H₄—CH=CH—CH₃ | —C₄H₉ | —F | —F |
| (729) | —C₂H₄—CH=CH—CH₃ | —C₅H₁₁ | —F | —F |
| (730) | —C₂H₄—CH=CH—CH₃ | —C₂H₄—CH=CH—CH₃ | —F | —F |
| (731) | —C₂H₄—CH=CH—CH₃ | —OC₂H₅ | —F | —F |
| (732) | —C₂H₄—CH=CH—CH₃ | —OC₃H₇ | —F | —F |
| (733) | —C₂H₄—CH=CH—CH₃ | —OC₄H₉ | —F | —F |
| (734) | —C₂H₄—CH=CH—CH₃ | —OC₅H₁₁ | —F | —F |
| (735) | —OC₂H₅ | —OC₂H₅ | —F | —F |
| (736) | —OC₂H₅ | —OC₃H₇ | —F | —F |
| (737) | —OC₂H₅ | —OC₄H₉ | —F | —F |
| (738) | —OC₂H₅ | —OC₅H₁₁ | —F | —F |
| (739) | —OC₃H₇ | —OC₃H₇ | —F | —F |
| (740) | —OC₃H₇ | —OC₄H₉ | —F | —F |
| (741) | —OC₃H₇ | —OC₅H₁₁ | —F | —F |
| (742) | —OC₄H₉ | —OC₄H₉ | —F | —F |
| (743) | —OC₄H₉ | —OC₅H₁₁ | —F | —F |
| (744) | —OC₅H₁₁ | —OC₅H₁₁ | —F | —F |
| (745) | —C₃H₇ | —C₃H₇ | —CF₃ | —CF₃ |
| (746) | —C₃H₇ | —C₄H₉ | —CF₃ | —CF₃ |
| (747) | —C₃H₇ | —C₅H₁₁ | —CF₃ | —CF₃ |
| (748) | —C₃H₇ | —OC₂H₅ | —CF₃ | —CF₃ |
| (749) | —C₃H₇ | —OC₃H₇ | —CF₃ | —CF₃ |
| (750) | —C₃H₇ | —OC₄H₉ | —CF₃ | —CF₃ |
| (751) | —C₃H₇ | —OC₅H₁₁ | —CF₃ | —CF₃ |
| (752) | —C₄H₉ | —C₄H₉ | —CF₃ | —CF₃ |
| (753) | —C₄H₉ | —C₅H₁₁ | —CF₃ | —CF₃ |
| (754) | —C₄H₉ | —OC₂H₅ | —CF₃ | —CF₃ |
| (755) | —C₄H₉ | —OC₃H₇ | —CF₃ | —CF₃ |
| (756) | —C₄H₉ | —OC₄H₉ | —CF₃ | —CF₃ |
| (757) | —C₄H₉ | —OC₅H₁₁ | —CF₃ | —CF₃ |
| (758) | —C₅H₁₁ | —C₅H₁₁ | —CF₃ | —CF₃ |
| (759) | —C₅H₁₁ | —OC₂H₅ | —CF₃ | —CF₃ |
| (760) | —C₅H₁₁ | —OC₃H₇ | —CF₃ | —CF₃ |
| (761) | —C₅H₁₁ | —OC₄H₉ | —CF₃ | —CF₃ |
| (762) | —C₅H₁₁ | —OC₅H₁₁ | —CF₃ | —CF₃ |
| (763) | —OC₂H₅ | —OC₂H₅ | —CF₃ | —CF₃ |
| (764) | —OC₂H₅ | —OC₃H₇ | —CF₃ | —CF₃ |
| (765) | —OC₂H₅ | —OC₄H₉ | —CF₃ | —CF₃ |
| (766) | —OC₂H₅ | —OC₅H₁₁ | —CF₃ | —CF₃ |
| (767) | —OC₃H₇ | —OC₃H₇ | —CF₃ | —CF₃ |
| (768) | —OC₃H₇ | —OC₄H₉ | —CF₃ | —CF₃ |
| (769) | —OC₃H₇ | —OC₅H₁₁ | —CF₃ | —CF₃ |
| (770) | —OC₄H₉ | —OC₄H₉ | —CF₃ | —CF₃ |
| (771) | —OC₄H₉ | —OC₅H₁₁ | —CF₃ | —CF₃ |
| (772) | —OC₅H₁₁ | —OC₅H₁₁ | —CF₃ | —CF₃ |

Fluorene compounds of the following formula

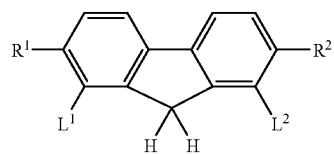

50

55 are obtained analogously to Example 3:

| | R¹ | R² | L¹ | L² |
|---|---|---|---|---|
| (800) | —C₃H₇ | —C₃H₇ | —H | —F |
| (801) | —C₃H₇ | —C₄H₉ | —H | —F |
| (802) | —C₃H₇ | —C₅H₁₁ | —H | —F |
| (803) | —C₃H₇ | —OC₂H₅ | —H | —F |
| (804) | —C₃H₇ | —OC₃H₇ | —H | —F |

-continued

|   | R¹ | R² | L¹ | L² |
|---|---|---|---|---|
| (805) | —C₃H₇ | —OC₄H₉ | —H | —F |
| (806) | —C₃H₇ | —OC₅H₁₁ | —H | —F |
| (807) | —C₄H₉ | —C₃H₇ | —H | —F |
| (808) | —C₄H₉ | —C₄H₉ | —H | —F |
| (809) | —C₄H₉ | —C₅H₁₁ | —H | —F |
| (810) | —C₄H₉ | —OC₂H₅ | —H | —F |
| (811) | —C₄H₉ | —OC₃H₇ | —H | —F |
| (812) | —C₄H₉ | —OC₄H₉ | —H | —F |
| (813) | —C₄H₉ | —OC₅H₁₁ | —H | —F |
| (814) | —C₅H₁₁ | —C₃H₇ | —H | —F |
| (815) | —C₅H₁₁ | —C₄H₉ | —H | —F |
| (816) | —C₅H₁₁ | —C₅H₁₁ | —H | —F |
| (817) | —C₅H₁₁ | —OC₂H₅ | —H | —F |
| (818) | —C₅H₁₁ | —OC₃H₇ | —H | —F |
| (819) | —C₅H₁₁ | —OC₄H₉ | —H | —F |
| (820) | —C₅H₁₁ | —OC₅H₁₁ | —H | —F |
| (821) | —CH=CH₂ | —C₃H₇ | —H | —F |
| (822) | —CH=CH₂ | —C₄H₉ | —H | —F |
| (823) | —CH=CH₂ | —C₅H₁₁ | —H | —F |
| (824) | —CH=CH₂ | —CH=CH₂ | —H | —F |
| (825) | —CH=CH₂ | —CH=CH—CH₃ | —H | —F |
| (826) | —CH=CH₂ | —CH₂—CH=CH—CH₃ | —H | —F |
| (827) | —CH=CH₂ | —C₂H₄—CH=CH₂ | —H | —F |
| (828) | —CH=CH₂ | —C₂H₄—CH=CH—CH₃ | —H | —F |
| (829) | —CH=CH₂ | —OC₂H₅ | —H | —F |
| (830) | —CH=CH₂ | —OC₃H₇ | —H | —F |
| (831) | —CH=CH₂ | —OC₄H₉ | —H | —F |
| (832) | —CH=CH₂ | —OC₅H₁₁ | —H | —F |
| (833) | —CH=CH—CH₃ | —C₃H₇ | —H | —F |
| (834) | —CH=CH—CH₃ | —C₄H₉ | —H | —F |
| (835) | —CH=CH—CH₃ | —C₅H₁₁ | —H | —F |
| (836) | —CH=CH—CH₃ | —CH=CH₂ | —H | —F |
| (837) | —CH=CH—CH₃ | —CH=CH—CH₃ | —H | —F |
| (838) | —CH=CH—CH₃ | —CH₂—CH=CH—CH₃ | —H | —F |
| (839) | —CH=CH—CH₃ | —C₂H₄—CH=CH₂ | —H | —F |
| (840) | —CH=CH—CH₃ | —C₂H₄—CH=CH—CH₃ | —H | —F |
| (841) | —CH=CH—CH₃ | —OC₂H₅ | —H | —F |
| (842) | —CH=CH—CH₃ | —OC₃H₇ | —H | —F |
| (843) | —CH=CH—CH₃ | —OC₄H₉ | —H | —F |
| (844) | —CH=CH—CH₃ | —OC₅H₁₁ | —H | —F |
| (845) | —CH₂—CH=CH—CH₃ | —C₃H₇ | —H | —F |
| (846) | —CH₂—CH=CH—CH₃ | —C₄H₉ | —H | —F |
| (847) | —CH₂—CH=CH—CH₃ | —C₅H₁₁ | —H | —F |
| (848) | —CH₂—CH=CH—CH₃ | —CH=CH₂ | —H | —F |
| (849) | —CH₂—CH=CH—CH₃ | —CH=CH—CH₃ | —H | —F |
| (850) | —CH₂—CH=CH—CH₃ | —CH₂—CH=CH—CH₃ | —H | —F |
| (851) | —CH₂—CH=CH—CH₃ | —C₂H₄—CH=CH₂ | —H | —F |
| (852) | —CH₂—CH=CH—CH₃ | —C₂H₄—CH=CH—CH₃ | —H | —F |
| (853) | —CH₂—CH=CH—CH₃ | —OC₂H₅ | —H | —F |
| (854) | —CH₂—CH=CH—CH₃ | —OC₃H₇ | —H | —F |
| (855) | —CH₂—CH=CH—CH₃ | —OC₄H₉ | —H | —F |
| (856) | —CH₂—CH=CH—CH₃ | —OC₅H₁₁ | —H | —F |
| (857) | —C₂H₄—CH=CH₂ | —C₃H₇ | —H | —F |
| (858) | —C₂H₄—CH=CH₂ | —C₄H₉ | —H | —F |
| (859) | —C₂H₄—CH=CH₂ | —C₅H₁₁ | —H | —F |
| (860) | —C₂H₄—CH=CH₂ | —CH=CH₂ | —H | —F |
| (861) | —C₂H₄—CH=CH₂ | —CH=CH—CH₃ | —H | —F |
| (862) | —C₂H₄—CH=CH₂ | —CH₂—CH=CH—CH₃ | —H | —F |
| (863) | —C₂H₄—CH=CH₂ | —C₂H₄—CH=CH₂ | —H | —F |
| (864) | —C₂H₄—CH=CH₂ | —C₂H₄—CH=CH—CH₃ | —H | —F |
| (865) | —C₂H₄—CH=CH₂ | —OC₂H₅ | —H | —F |
| (866) | —C₂H₄—CH=CH₂ | —OC₃H₇ | —H | —F |
| (867) | —C₂H₄—CH=CH₂ | —OC₄H₉ | —H | —F |
| (868) | —C₂H₄—CH=CH₂ | —OC₅H₁₁ | —H | —F |
| (869) | —C₂H₄—CH=CH—CH₃ | —C₃H₇ | —H | —F |
| (870) | —C₂H₄—CH=CH—CH₃ | —C₄H₉ | —H | —F |
| (871) | —C₂H₄—CH=CH—CH₃ | —C₅H₁₁ | —H | —F |
| (872) | —C₂H₄—CH=CH—CH₃ | —CH=CH₂ | —H | —F |
| (873) | —C₂H₄—CH=CH—CH₃ | —CH=CH—CH₃ | —H | —F |
| (874) | —C₂H₄—CH=CH—CH₃ | —CH₂—CH=CH—CH₃ | —H | —F |
| (875) | —C₂H₄—CH=CH—CH₃ | —C₂H₄—CH=CH₂ | —H | —F |
| (876) | —C₂H₄—CH=CH—CH₃ | —C₂H₄—CH=CH—CH₃ | —H | —F |
| (877) | —C₂H₄—CH=CH—CH₃ | —OC₂H₅ | —H | —F |
| (878) | —C₂H₄—CH=CH—CH₃ | —OC₃H₇ | —H | —F |
| (879) | —C₂H₄—CH=CH—CH₃ | —OC₄H₉ | —H | —F |
| (880) | —C₂H₄—CH=CH—CH₃ | —OC₅H₁₁ | —H | —F |
| (881) | —OC₂H₅ | —C₃H₇ | —H | —F |

-continued

|  | R¹ | R² | L¹ | L² |
|---|---|---|---|---|
| (882) | —OC$_2$H$_5$ | —C$_4$H$_9$ | —H | —F |
| (883) | —OC$_2$H$_5$ | —C$_5$H$_{11}$ | —H | —F |
| (884) | —OC$_2$H$_5$ | —OC$_2$H$_5$ | —H | —F |
| (885) | —OC$_2$H$_5$ | —OC$_3$H$_7$ | —H | —F |
| (886) | —OC$_2$H$_5$ | —OC$_4$H$_9$ | —H | —F |
| (887) | —OC$_2$H$_5$ | —OC$_5$H$_{11}$ | —H | —F |
| (888) | —OC$_3$H$_7$ | —C$_3$H$_7$ | —H | —F |
| (889) | —OC$_3$H$_7$ | —C$_4$H$_9$ | —H | —F |
| (890) | —OC$_3$H$_7$ | —C$_5$H$_{11}$ | —H | —F |
| (891) | —OC$_3$H$_7$ | —OC$_2$H$_5$ | —H | —F |
| (892) | —OC$_3$H$_7$ | —OC$_3$H$_7$ | —H | —F |
| (893) | —OC$_3$H$_7$ | —OC$_4$H$_9$ | —H | —F |
| (894) | —OC$_3$H$_7$ | —OC$_5$H$_{11}$ | —H | —F |
| (895) | —OC$_4$H$_9$ | —C$_3$H$_7$ | —H | —F |
| (896) | —OC$_4$H$_9$ | —C$_4$H$_9$ | —H | —F |
| (897) | —OC$_4$H$_9$ | —C$_5$H$_{11}$ | —H | —F |
| (898) | —OC$_4$H$_9$ | —OC$_2$H$_5$ | —H | —F |
| (899) | —OC$_4$H$_9$ | —OC$_3$H$_7$ | —H | —F |
| (900) | —OC$_4$H$_9$ | —OC$_4$H$_9$ | —H | —F |
| (901) | —OC$_4$H$_9$ | —OC$_5$H$_{11}$ | —H | —F |
| (902) | —OC$_5$H$_{11}$ | —C$_3$H$_7$ | —H | —F |
| (903) | —OC$_5$H$_{11}$ | —C$_4$H$_9$ | —H | —F |
| (904) | —OC$_5$H$_{11}$ | —C$_5$H$_{11}$ | —H | —F |
| (905) | —OC$_5$H$_{11}$ | —OC$_2$H$_5$ | —H | —F |
| (906) | —OC$_5$H$_{11}$ | —OC$_3$H$_7$ | —H | —F |
| (907) | —OC$_5$H$_{11}$ | —OC$_4$H$_9$ | —H | —F |
| (908) | —OC$_5$H$_{11}$ | —OC$_5$H$_{11}$ | —H | —F |
| (909) | —C$_3$H$_7$ | —C$_3$H$_7$ | —H | —CF$_3$ |
| (910) | —C$_3$H$_7$ | —C$_4$H$_9$ | —H | —CF$_3$ |
| (911) | —C$_3$H$_7$ | —C$_5$H$_{11}$ | —H | —CF$_3$ |
| (912) | —C$_3$H$_7$ | —OC$_2$H$_5$ | —H | —CF$_3$ |
| (913) | —C$_3$H$_7$ | —OC$_3$H$_7$ | —H | —CF$_3$ |
| (914) | —C$_3$H$_7$ | —OC$_4$H$_9$ | —H | —CF$_3$ |
| (915) | —C$_3$H$_7$ | —OC$_5$H$_{11}$ | —H | —CF$_3$ |
| (916) | —C$_4$H$_9$ | —C$_3$H$_7$ | —H | —CF$_3$ |
| (917) | —C$_4$H$_9$ | —C$_4$H$_9$ | —H | —CF$_3$ |
| (918) | —C$_4$H$_9$ | —C$_5$H$_{11}$ | —H | —CF$_3$ |
| (919) | —C$_4$H$_9$ | —OC$_2$H$_5$ | —H | —CF$_3$ |
| (920) | —C$_4$H$_9$ | —OC$_3$H$_7$ | —H | —CF$_3$ |
| (921) | —C$_4$H$_9$ | —OC$_4$H$_9$ | —H | —CF$_3$ |
| (922) | —C$_4$H$_9$ | —OC$_5$H$_{11}$ | —H | —CF$_3$ |
| (923) | —C$_5$H$_{11}$ | —C$_3$H$_7$ | —H | —CF$_3$ |
| (924) | —C$_5$H$_{11}$ | —C$_4$H$_9$ | —H | —CF$_3$ |
| (925) | —C$_5$H$_{11}$ | —C$_5$H$_{11}$ | —H | —CF$_3$ |
| (926) | —C$_5$H$_{11}$ | —OC$_2$H$_5$ | —H | —CF$_3$ |
| (927) | —C$_5$H$_{11}$ | —OC$_3$H$_7$ | —H | —CF$_3$ |
| (928) | —C$_5$H$_{11}$ | —OC$_4$H$_9$ | —H | —CF$_3$ |
| (929) | —C$_5$H$_{11}$ | —OC$_5$H$_{11}$ | —H | —CF$_3$ |
| (930) | —OC$_2$H$_5$ | —C$_3$H$_7$ | —H | —CF$_3$ |
| (931) | —OC$_2$H$_5$ | —C$_4$H$_9$ | —H | —CF$_3$ |
| (932) | —OC$_2$H$_5$ | —C$_5$H$_{11}$ | —H | —CF$_3$ |
| (933) | —OC$_2$H$_5$ | —OC$_2$H$_5$ | —H | —CF$_3$ |
| (934) | —OC$_2$H$_5$ | —OC$_3$H$_7$ | —H | —CF$_3$ |
| (935) | —OC$_2$H$_5$ | —OC$_4$H$_9$ | —H | —CF$_3$ |
| (936) | —OC$_2$H$_5$ | —OC$_5$H$_{11}$ | —H | —CF$_3$ |
| (937) | —OC$_3$H$_7$ | —C$_3$H$_7$ | —H | —CF$_3$ |
| (938) | —OC$_3$H$_7$ | —C$_4$H$_9$ | —H | —CF$_3$ |
| (939) | —OC$_3$H$_7$ | —C$_5$H$_{11}$ | —H | —CF$_3$ |
| (940) | —OC$_3$H$_7$ | —OC$_2$H$_5$ | —H | —CF$_3$ |
| (941) | —OC$_3$H$_7$ | —OC$_3$H$_7$ | —H | —CF$_3$ |
| (942) | —OC$_3$H$_7$ | —OC$_4$H$_9$ | —H | —CF$_3$ |
| (943) | —OC$_3$H$_7$ | —OC$_5$H$_{11}$ | —H | —CF$_3$ |
| (944) | —OC$_4$H$_9$ | —C$_3$H$_7$ | —H | —CF$_3$ |
| (945) | —OC$_4$H$_9$ | —C$_4$H$_9$ | —H | —CF$_3$ |
| (946) | —OC$_4$H$_9$ | —C$_5$H$_{11}$ | —H | —CF$_3$ |
| (947) | —OC$_4$H$_9$ | —OC$_2$H$_5$ | —H | —CF$_3$ |
| (948) | —OC$_4$H$_9$ | —OC$_3$H$_7$ | —H | —CF$_3$ |
| (949) | —OC$_4$H$_9$ | —OC$_4$H$_9$ | —H | —CF$_3$ |
| (950) | —OC$_4$H$_9$ | —OC$_5$H$_{11}$ | —H | —CF$_3$ |
| (951) | —OC$_5$H$_{11}$ | —C$_3$H$_7$ | —H | —CF$_3$ |
| (952) | —OC$_5$H$_{11}$ | —C$_4$H$_9$ | —H | —CF$_3$ |
| (953) | —OC$_5$H$_{11}$ | —C$_5$H$_{11}$ | —H | —CF$_3$ |
| (954) | —OC$_5$H$_{11}$ | —OC$_2$H$_5$ | —H | —CF$_3$ |
| (955) | —OC$_5$H$_{11}$ | —OC$_3$H$_7$ | —H | —CF$_3$ |
| (956) | —OC$_5$H$_{11}$ | —OC$_4$H$_9$ | —H | —CF$_3$ |
| (957) | —OC$_5$H$_{11}$ | —OC$_5$H$_{11}$ | —H | —CF$_3$ |
| (958) | —C$_3$H$_7$ | —C$_3$H$_7$ | —F | —CF$_3$ |

-continued

| | R¹ | R² | L¹ | L² |
|---|---|---|---|---|
| (959) | —C$_3$H$_7$ | —C$_4$H$_9$ | —F | —CF$_3$ |
| (960) | —C$_3$H$_7$ | —C$_5$H$_{11}$ | —F | —CF$_3$ |
| (961) | —C$_3$H$_7$ | —OC$_2$H$_5$ | —F | —CF$_3$ |
| (962) | —C$_3$H$_7$ | —OC$_3$H$_7$ | —F | —CF$_3$ |
| (963) | —C$_3$H$_7$ | —OC$_4$H$_9$ | —F | —CF$_3$ |
| (964) | —C$_3$H$_7$ | —OC$_5$H$_{11}$ | —F | —CF$_3$ |
| (965) | —C$_4$H$_9$ | —C$_3$H$_7$ | —F | —CF$_3$ |
| (966) | —C$_4$H$_9$ | —C$_4$H$_9$ | —F | —CF$_3$ |
| (967) | —C$_4$H$_9$ | —C$_5$H$_{11}$ | —F | —CF$_3$ |
| (968) | —C$_4$H$_9$ | —OC$_2$H$_5$ | —F | —CF$_3$ |
| (969) | —C$_4$H$_9$ | —OC$_3$H$_7$ | —F | —CF$_3$ |
| (970) | —C$_4$H$_9$ | —OC$_4$H$_9$ | —F | —CF$_3$ |
| (971) | —C$_4$H$_9$ | —OC$_5$H$_{11}$ | —F | —CF$_3$ |
| (972) | —C$_5$H$_{11}$ | —C$_3$H$_7$ | —F | —CF$_3$ |
| (973) | —C$_5$H$_{11}$ | —C$_4$H$_9$ | —F | —CF$_3$ |
| (974) | —C$_5$H$_{11}$ | —C$_5$H$_{11}$ | —F | —CF$_3$ |
| (975) | —C$_5$H$_{11}$ | —OC$_2$H$_5$ | —F | —CF$_3$ |
| (976) | —C$_5$H$_{11}$ | —OC$_3$H$_7$ | —F | —CF$_3$ |
| (977) | —C$_5$H$_{11}$ | —OC$_4$H$_9$ | —F | —CF$_3$ |
| (978) | —C$_5$H$_{11}$ | —OC$_5$H$_{11}$ | —F | —CF$_3$ |
| (979) | —CH=CH$_2$ | —C$_3$H$_7$ | —F | —CF$_3$ |
| (980) | —CH=CH$_2$ | —C$_4$H$_9$ | —F | —CF$_3$ |
| (981) | —CH=CH$_2$ | —C$_5$H$_{11}$ | —F | —CF$_3$ |
| (982) | —CH=CH$_2$ | —CH=CH$_2$ | —F | —CF$_3$ |
| (983) | —CH=CH$_2$ | —CH=CH—CH$_3$ | —F | —CF$_3$ |
| (984) | —CH=CH$_2$ | —CH$_2$—CH=CH—CH$_3$ | —F | —CF$_3$ |
| (985) | —CH=CH$_2$ | —C$_2$H$_4$—CH=CH$_2$ | —F | —CF$_3$ |
| (986) | —CH=CH$_2$ | —C$_2$H$_4$—CH=CH—CH$_3$ | —F | —CF$_3$ |
| (987) | —CH=CH$_2$ | —OC$_2$H$_5$ | —F | —CF$_3$ |
| (988) | —CH=CH$_2$ | —OC$_3$H$_7$ | —F | —CF$_3$ |
| (989) | —CH=CH$_2$ | —OC$_4$H$_9$ | —F | —CF$_3$ |
| (990) | —CH=CH$_2$ | —OC$_5$H$_{11}$ | —F | —CF$_3$ |
| (991) | —CH=CH—CH$_3$ | —C$_3$H$_7$ | —F | —CF$_3$ |
| (992) | —CH=CH—CH$_3$ | —C$_4$H$_9$ | —F | —CF$_3$ |
| (993) | —CH=CH—CH$_3$ | —C$_5$H$_{11}$ | —F | —CF$_3$ |
| (994) | —CH=CH—CH$_3$ | —CH=CH$_2$ | —F | —CF$_3$ |
| (995) | —CH=CH—CH$_3$ | —CH=CH—CH$_3$ | —F | —CF$_3$ |
| (996) | —CH=CH—CH$_3$ | —CH$_2$—CH=CH—CH$_3$ | —F | —CF$_3$ |
| (997) | —CH=CH—CH$_3$ | —C$_2$H$_4$—CH=CH$_2$ | —F | —CF$_3$ |
| (998) | —CH=CH—CH$_3$ | —C$_2$H$_4$—CH=CH—CH$_3$ | —F | —CF$_3$ |
| (999) | —CH=CH—CH$_3$ | —OC$_2$H$_5$ | —F | —CF$_3$ |
| (1000) | —CH=CH—CH$_3$ | —OC$_3$H$_7$ | —F | —CF$_3$ |
| (1001) | —CH=CH—CH$_3$ | —OC$_4$H$_9$ | —F | —CF$_3$ |
| (1002) | —CH=CH—CH$_3$ | —OC$_5$H$_{11}$ | —F | —CF$_3$ |
| (1003) | —CH$_2$—CH=CH—CH$_3$ | —C$_3$H$_7$ | —F | —CF$_3$ |
| (1004) | —CH$_2$—CH=CH—CH$_3$ | —C$_4$H$_9$ | —F | —CF$_3$ |
| (1005) | —CH$_2$—CH=CH—CH$_3$ | —C$_5$H$_{11}$ | —F | —CF$_3$ |
| (1006) | —CH$_2$—CH=CH—CH$_3$ | —CH=CH$_2$ | —F | —CF$_3$ |
| (1007) | —CH$_2$—CH=CH—CH$_3$ | —CH=CH—CH$_3$ | —F | —CF$_3$ |
| (1008) | —CH$_2$—CH=CH—CH$_3$ | —CH$_2$—CH=CH—CH$_3$ | —F | —CF$_3$ |
| (1009) | —CH$_2$—CH=CH—CH$_3$ | —C$_2$H$_4$—CH=CH$_2$ | —F | —CF$_3$ |
| (1010) | —CH$_2$—CH=CH—CH$_3$ | —C$_2$H$_4$—CH=CH—CH$_3$ | —F | —CF$_3$ |
| (1011) | —CH$_2$—CH=CH—CH$_3$ | —OC$_2$H$_5$ | —F | —CF$_3$ |
| (1012) | —CH$_2$—CH=CH—CH$_3$ | —OC$_3$H$_7$ | —F | —CF$_3$ |
| (1013) | —CH$_2$—CH=CH—CH$_3$ | —OC$_4$H$_9$ | —F | —CF$_3$ |
| (1014) | —CH$_2$—CH=CH—CH$_3$ | —OC$_5$H$_{11}$ | —F | —CF$_3$ |
| (1015) | —C$_2$H$_4$—CH=CH$_2$ | —C$_3$H$_7$ | —F | —CF$_3$ |
| (1016) | —C$_2$H$_4$—CH=CH$_2$ | —C$_4$H$_9$ | —F | —CF$_3$ |
| (1017) | —C$_2$H$_4$—CH=CH$_2$ | —C$_5$H$_{11}$ | —F | —CF$_3$ |
| (1018) | —C$_2$H$_4$—CH=CH$_2$ | —CH=CH$_2$ | —F | —CF$_3$ |
| (1019) | —C$_2$H$_4$—CH=CH$_2$ | —CH=CH—CH$_3$ | —F | —CF$_3$ |
| (1020) | —C$_2$H$_4$—CH=CH$_2$ | —CH$_2$—CH=CH—CH$_3$ | —F | —CF$_3$ |
| (1021) | —C$_2$H$_4$—CH=CH$_2$ | —C$_2$H$_4$—CH=CH$_2$ | —F | —CF$_3$ |
| (1022) | —C$_2$H$_4$—CH=CH$_2$ | —C$_2$H$_4$—CH=CH—CH$_3$ | —F | —CF$_3$ |
| (1023) | —C$_2$H$_4$—CH=CH$_2$ | —OC$_2$H$_5$ | —F | —CF$_3$ |
| (1024) | —C$_2$H$_4$—CH=CH$_2$ | —OC$_3$H$_7$ | —F | —CF$_3$ |
| (1025) | —C$_2$H$_4$—CH=CH$_2$ | —OC$_4$H$_9$ | —F | —CF$_3$ |
| (1026) | —C$_2$H$_4$—CH=CH$_2$ | —OC$_5$H$_{11}$ | —F | —CF$_3$ |
| (1027) | —C$_2$H$_4$—CH=CH—CH$_3$ | —C$_3$H$_7$ | —F | —CF$_3$ |
| (1028) | —C$_2$H$_4$—CH=CH—CH$_3$ | —C$_4$H$_9$ | —F | —CF$_3$ |
| (1029) | —C$_2$H$_4$—CH=CH—CH$_3$ | —C$_5$H$_{11}$ | —F | —CF$_3$ |
| (1030) | —C$_2$H$_4$—CH=CH—CH$_3$ | —CH=CH$_2$ | —F | —CF$_3$ |
| (1031) | —C$_2$H$_4$—CH=CH—CH$_3$ | —CH=CH—CH$_3$ | —F | —CF$_3$ |
| (1032) | —C$_2$H$_4$—CH=CH—CH$_3$ | —CH$_2$—CH=CH—CH$_3$ | —F | —CF$_3$ |
| (1033) | —C$_2$H$_4$—CH=CH—CH$_3$ | —C$_2$H$_4$—CH=CH$_2$ | —F | —CF$_3$ |
| (1034) | —C$_2$H$_4$—CH=CH—CH$_3$ | —C$_2$H$_4$—CH=CH—CH$_3$ | —F | —CF$_3$ |
| (1035) | —C$_2$H$_4$—CH=CH—CH$_3$ | —OC$_2$H$_5$ | —F | —CF$_3$ |

-continued

| | R¹ | R² | L¹ | L² | |
|---|---|---|---|---|---|
| (1036) | —C₂H₄—CH=CH—CH₃ | —OC₃H₇ | —F | —CF₃ | |
| (1037) | —C₂H₄—CH=CH—CH₃ | —OC₄H₉ | —F | —CF₃ | |
| (1038) | —C₂H₄—CH=CH—CH₃ | —OC₅H₁₁ | —F | —CF₃ | |
| (1039) | —OC₂H₅ | —C₃H₇ | —F | —CF₃ | |
| (1040) | —OC₂H₅ | —C₄H₉ | —F | —CF₃ | |
| (1041) | —OC₂H₅ | —C₅H₁₁ | —F | —CF₃ | Δε = −7.0; Δn = 0.176 |
| (1042) | —OC₂H₅ | —OC₂H₅ | —F | —CF₃ | |
| (1043) | —OC₂H₅ | —OC₃H₇ | —F | —CF₃ | |
| (1044) | —OC₂H₅ | —OC₄H₉ | —F | —CF₃ | |
| (1045) | —OC₂H₅ | —OC₅H₁₁ | —F | —CF₃ | |
| (1046) | —OC₃H₇ | —C₃H₇ | —F | —CF₃ | |
| (1047) | —OC₃H₇ | —C₄H₉ | —F | —CF₃ | |
| (1048) | —OC₃H₇ | —C₅H₁₁ | —F | —CF₃ | |
| (1049) | —OC₃H₇ | —OC₂H₅ | —F | —CF₃ | |
| (1050) | —OC₃H₇ | —OC₃H₇ | —F | —CF₃ | |
| (1051) | —OC₃H₇ | —OC₄H₉ | —F | —CF₃ | |
| (1052) | —OC₃H₇ | —OC₅H₁₁ | —F | —CF₃ | |
| (1053) | —OC₄H₉ | —C₃H₇ | —F | —CF₃ | |
| (1054) | —OC₄H₉ | —C₄H₉ | —F | —CF₃ | |
| (1055) | —OC₄H₉ | —C₅H₁₁ | —F | —CF₃ | |
| (1056) | —OC₄H₉ | —OC₂H₅ | —F | —CF₃ | |
| (1057) | —OC₄H₉ | —OC₃H₇ | —F | —CF₃ | |
| (1058) | —OC₄H₉ | —OC₄H₉ | —F | —CF₃ | |
| (1059) | —OC₄H₉ | —OC₅H₁₁ | —F | —CF₃ | |
| (1060) | —OC₅H₁₁ | —C₃H₇ | —F | —CF₃ | |
| (1061) | —OC₅H₁₁ | —C₄H₉ | —F | —CF₃ | |
| (1062) | —OC₅H₁₁ | —C₅H₁₁ | —F | —CF₃ | |
| (1063) | —OC₅H₁₁ | —OC₂H₅ | —F | —CF₃ | |
| (1064) | —OC₅H₁₁ | —OC₃H₇ | —F | —CF₃ | |
| (1065) | —OC₅H₁₁ | —OC₄H₉ | —F | —CF₃ | |
| (1066) | —OC₅H₁₁ | —OC₅H₁₁ | —F | —CF₃ | |
| (1067) | —C₃H₇ | —C₃H₇ | —F | —F | |
| (1068) | —C₃H₇ | —C₄H₉ | —F | —F | |
| (1069) | —C₃H₇ | —C₅H₁₁ | —F | —F | |
| (1070) | —C₃H₇ | —OC₂H₅ | —F | —F | |
| (1071) | —C₃H₇ | —OC₃H₇ | —F | —F | |
| (1072) | —C₃H₇ | —OC₄H₉ | —F | —F | |
| (1073) | —C₃H₇ | —OC₅H₁₁ | —F | —F | |
| (1074) | —C₄H₉ | —C₄H₉ | —F | —F | |
| (1075) | —C₄H₉ | —C₅H₁₁ | —F | —F | |
| (1076) | —C₄H₉ | —OC₂H₅ | —F | —F | |
| (1077) | —C₄H₉ | —OC₃H₇ | —F | —F | |
| (1078) | —C₄H₉ | —OC₄H₉ | —F | —F | |
| (1079) | —C₄H₉ | —OC₅H₁₁ | —F | —F | |
| (1080) | —C₅H₁₁ | —C₅H₁₁ | —F | —F | |
| (1081) | —C₅H₁₁ | —OC₂H₅ | —F | —F | |
| (1082) | —C₅H₁₁ | —OC₃H₇ | —F | —F | |
| (1083) | —C₅H₁₁ | —OC₄H₉ | —F | —F | |
| (1084) | —C₅H₁₁ | —OC₅H₁₁ | —F | —F | |
| (1085) | —CH=CH₂ | —C₃H₇ | —F | —F | |
| (1086) | —CH=CH₂ | —C₄H₉ | —F | —F | |
| (1087) | —CH=CH₂ | —C₅H₁₁ | —F | —F | |
| (1088) | —CH=CH₂ | —CH=CH₂ | —F | —F | |
| (1089) | —CH=CH₂ | —CH=CH—CH₃ | —F | —F | |
| (1090) | —CH=CH₂ | —CH₂—CH=CH—CH₃ | —F | —F | |
| (1091) | —CH=CH₂ | —C₂H₄—CH=CH₂ | —F | —F | |
| (1092) | —CH=CH₂ | —C₂H₄—CH=CH—CH₃ | —F | —F | |
| (1093) | —CH=CH₂ | —OC₂H₅ | —F | —F | |
| (1094) | —CH=CH₂ | —OC₃H₇ | —F | —F | |
| (1095) | —CH=CH₂ | —OC₄H₉ | —F | —F | |
| (1096) | —CH=CH₂ | —OC₅H₁₁ | —F | —F | |
| (1097) | —CH=CH—CH₃ | —C₃H₇ | —F | —F | |
| (1098) | —CH=CH—CH₃ | —C₄H₉ | —F | —F | |
| (1099) | —CH=CH—CH₃ | —C₅H₁₁ | —F | —F | |
| (1100) | —CH=CH—CH₃ | —CH=CH—CH₃ | —F | —F | |
| (1101) | —CH=CH—CH₃ | —CH₂—CH=CH—CH₃ | —F | —F | |
| (1102) | —CH=CH—CH₃ | —C₂H₄—CH=CH₂ | —F | —F | |
| (1103) | —CH=CH—CH₃ | —C₂H₄—CH=CH—CH₃ | —F | —F | |
| (1104) | —CH=CH—CH₃ | —OC₂H₅ | —F | —F | |
| (1105) | —CH=CH—CH₃ | —OC₃H₇ | —F | —F | |
| (1106) | —CH=CH—CH₃ | —OC₄H₉ | —F | —F | |
| (1107) | —CH=CH—CH₃ | —OC₅H₁₁ | —F | —F | |
| (1108) | —CH₂—CH=CH—CH₃ | —C₃H₇ | —F | —F | |

-continued

| | R¹ | R² | L¹ | L² |
|---|---|---|---|---|
| (1109) | —CH₂—CH=CH—CH₃ | —C₄H₉ | —F | —F |
| (1110) | —CH₂—CH=CH—CH₃ | —C₅H₁₁ | —F | —F |
| (1111) | —CH₂—CH=CH—CH₃ | —CH₂—CH=CH—CH₃ | —F | —F |
| (1112) | —CH₂—CH=CH—CH₃ | —C₂H₄—CH=CH₂ | —F | —F |
| (1113) | —CH₂—CH=CH—CH₃ | —C₂H₄—CH=CH—CH₃ | —F | —F |
| (1114) | —CH₂—CH=CH—CH₃ | —OC₂H₅ | —F | —F |
| (1115) | —CH₂—CH=CH—CH₃ | —OC₃H₇ | —F | —F |
| (1116) | —CH₂—CH=CH—CH₃ | —OC₄H₉ | —F | —F |
| (1117) | —CH₂—CH=CH—CH₃ | —OC₅H₁₁ | —F | —F |
| (1118) | —C₂H₄—CH=CH₂ | —C₃H₇ | —F | —F |
| (1119) | —C₂H₄—CH=CH₂ | —C₄H₉ | —F | —F |
| (1120) | —C₂H₄—CH=CH₂ | —C₅H₁₁ | —F | —F |
| (1121) | —C₂H₄—CH=CH₂ | —C₂H₄—CH=CH₂ | —F | —F |
| (1122) | —C₂H₄—CH=CH₂ | —C₂H₄—CH=CH—CH₃ | —F | —F |
| (1123) | —C₂H₄—CH=CH₂ | —OC₂H₅ | —F | —F |
| (1124) | —C₂H₄—CH=CH₂ | —OC₃H₇ | —F | —F |
| (1125) | —C₂H₄—CH=CH₂ | —OC₄H₉ | —F | —F |
| (1126) | —C₂H₄—CH=CH₂ | —OC₅H₁₁ | —F | —F |
| (1127) | —C₂H₄—CH=CH—CH₃ | —C₃H₇ | —F | —F |
| (1128) | —C₂H₄—CH=CH—CH₃ | —C₄H₉ | —F | —F |
| (1129) | —C₂H₄—CH=CH—CH₃ | —C₅H₁₁ | —F | —F |
| (1130) | —C₂H₄—CH=CH—CH₃ | —C₂H₄—CH=CH—CH₃ | —F | —F |
| (1131) | —C₂H₄—CH=CH—CH₃ | —OC₂H₅ | —F | —F |
| (1132) | —C₂H₄—CH=CH—CH₃ | —OC₃H₇ | —F | —F |
| (1133) | —C₂H₄—CH=CH—CH₃ | —OC₄H₉ | —F | —F |
| (1134) | —C₂H₄—CH=CH—CH₃ | —OC₅H₁₁ | —F | —F |
| (1135) | —OC₂H₅ | —OC₂H₅ | —F | —F |
| (1136) | —OC₂H₅ | —OC₃H₇ | —F | —F |
| (1137) | —OC₂H₅ | —OC₄H₉ | —F | —F |
| (1138) | —OC₂H₅ | —OC₅H₁₁ | —F | —F |
| (1139) | —OC₃H₇ | —OC₃H₇ | —F | —F |
| (1140) | —OC₃H₇ | —OC₄H₉ | —F | —F |
| (1141) | —OC₃H₇ | —OC₅H₁₁ | —F | —F |
| (1142) | —OC₄H₉ | —OC₄H₉ | —F | —F |
| (1143) | —OC₄H₉ | —OC₅H₁₁ | —F | —F |
| (1144) | —OC₅H₁₁ | —OC₅H₁₁ | —F | —F |
| (1145) | —C₃H₇ | —C₃H₇ | —CF₃ | —CF₃ |
| (1146) | —C₃H₇ | —C₄H₉ | —CF₃ | —CF₃ |
| (1147) | —C₃H₇ | —C₅H₁₁ | —CF₃ | —CF₃ |
| (1148) | —C₃H₇ | —OC₂H₅ | —CF₃ | —CF₃ |
| (1149) | —C₃H₇ | —OC₃H₇ | —CF₃ | —CF₃ |
| (1150) | —C₃H₇ | —OC₄H₉ | —CF₃ | —CF₃ |
| (1151) | —C₃H₇ | —OC₅H₁₁ | —CF₃ | —CF₃ |
| (1152) | —C₄H₉ | —C₄H₉ | —CF₃ | —CF₃ |
| (1153) | —C₄H₉ | —C₅H₁₁ | —CF₃ | —CF₃ |
| (1154) | —C₄H₉ | —OC₂H₅ | —CF₃ | —CF₃ |
| (1155) | —C₄H₉ | —OC₃H₇ | —CF₃ | —CF₃ |
| (1156) | —C₄H₉ | —OC₄H₉ | —CF₃ | —CF₃ |
| (1157) | —C₄H₉ | —OC₅H₁₁ | —CF₃ | —CF₃ |
| (1158) | —C₅H₁₁ | —C₅H₁₁ | —CF₃ | —CF₃ |
| (1159) | —C₅H₁₁ | —OC₂H₅ | —CF₃ | —CF₃ |
| (1160) | —C₅H₁₁ | —OC₃H₇ | —CF₃ | —CF₃ |
| (1161) | —C₅H₁₁ | —OC₄H₉ | —CF₃ | —CF₃ |
| (1162) | —C₅H₁₁ | —OC₅H₁₁ | —CF₃ | —CF₃ |
| (1163) | —OC₂H₅ | —OC₂H₅ | —CF₃ | —CF₃ |
| (1164) | —OC₂H₅ | —OC₃H₇ | —CF₃ | —CF₃ |
| (1165) | —OC₂H₅ | —OC₄H₉ | —CF₃ | —CF₃ |
| (1166) | —OC₂H₅ | —OC₅H₁₁ | —CF₃ | —CF₃ |
| (1167) | —OC₃H₇ | —OC₃H₇ | —CF₃ | —CF₃ |
| (1168) | —OC₃H₇ | —OC₄H₉ | —CF₃ | —CF₃ |
| (1169) | —OC₃H₇ | —OC₅H₁₁ | —CF₃ | —CF₃ |
| (1170) | —OC₄H₉ | —OC₄H₉ | —CF₃ | —CF₃ |
| (1171) | —OC₄H₉ | —OC₅H₁₁ | —CF₃ | —CF₃ |
| (1172) | —OC₅H₁₁ | —OC₅H₁₁ | —CF₃ | —CF₃ |

What is claimed is:

1. A fluorene compound of formula I

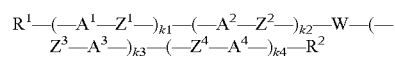

I in which

W is the

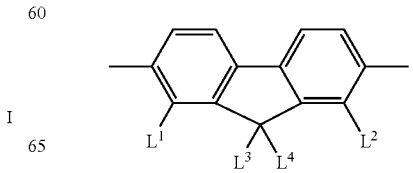

group, $L^1$ and $L^2$, independently of one another, are H, F, Cl, —CH$_2$F, —CHF$_2$ or —CF$_3$, with the proviso that $L^1$ and $L^2$ are not both H, $L^3$ and $L^4$, independently of one another, are H or F, wherein one of $L^3$ and $L^4$ is H and the other is F, $R^1$ and $R^2$, independently of one another, are H, halogen, —CN, —NCS, —SF$_5$ or alkyl having from 1 to 18 carbon atoms, in which, in addition, one or two non-adjacent —CH$_2$— groups may be replaced by —O—, —S—, —CO—, —O—CO—, —CO—O—, —E— and/or —C≡C—and/or in which, in addition, one or more H atoms may be replaced by halogen and/or —CN, E is CR$^4$=CR$^5$ or CHR$^4$—CHR$^5$, $R^4$ and $R^5$ are each, independently of one another, H, alkyl having 1–6 carbon atoms, F, Cl, CF$_3$ or CN, $A^1$, $A^2$, $A^3$ and $A^4$ are each, independently of one another, 1,4-phenylene, in which one or more CH groups may be replaced by N, 1,4-cyclohexylene, in which one or two non-adjacent CH$_2$ groups may be replaced by O and/or S, 1,4-cyclohexenylene, 1,4-bicyclo[2.2.2]oc-tylene, piperidine-1,4-diyl, naphthalene-2,6-diyl, decahydronaphthalene-2,6-diyl or 1,2,3,4-tetrahydronaphthalene-2,6-diyl, where, in the meanings given for $A^1$, $A^2$, $A^3$ and $A^4$, one or more H atoms may be substituted by halogen, —CN and/or alkyl having from 1 to 6 carbon atoms, in which one or more H atoms may be replaced by halogen or —CN, and/or in which one or more non-adjacent —CH$_2$— groups may be replaced, independently of one another, by —CO—, —O—CO—, —CO—O—, —O—, —S—, —CH=CH— or —C≡C—, and $Z^1$, $Z^2$, $Z^3$ and $Z^4$, independently of one another, are —O—CO—, —CO—O—, —CH$_2$—O—, —CF$_2$—O—, —O—CH$_2$—, —O—CF$_2$—, —C$_2$H$_4$—, —CH$_2$—CF$_2$—, —CF$_2$—CH$_2$—, —CF$_2$—CF$_2$—, —CH=CH—, —CF=CH—, —CH=CF—, —CF=CF—, —C≡C— or a single bond, k1, k2, k3 and k4, independently of one another, are 0, 1 or 2.

2. A fluorene compound according to claim 1, wherein said compound is of formula Ia $$R^1\text{—}W\text{—}R^2 \qquad \text{Ia.}$$

3. A fluorene compound according to claim 1, wherein said compound is of formula Ib $$R^1\text{—}A^1\text{—}Z^1\text{—}W\text{—}R^2 \qquad \text{Ib.}$$

4. A fluorene compound according to claim 1, wherein said compound is of formula Ic or Id $$R^1\text{—}A^1\text{—}Z^1\text{—}A^2\text{—}Z^2\text{—}W\text{—}R^2 \qquad \text{Ic}$$

$$R^1\text{—}A^1\text{—}Z^1\text{—}W\text{—}Z^3\text{—}A^3\text{—}R^2 \qquad \text{Id.}$$

5. A fluorene compound according to claim 1, wherein $$R^1\text{—}(\text{—}A^1\text{—}Z^1\text{—})_{k1}\text{—}(\text{—}A^2\text{—}Z^2\text{—})_{k2}\text{—} \text{ and}$$

$$\text{—}(\text{—}Z^3\text{—}A^3\text{—})_{k3}\text{—}(\text{—}Z^4\text{—}A^4\text{—})_{k4}\text{—}R^2$$

are each selected so that the fluorene compound has a dielectric anisotropy Δε of less than or equal to −6.0.

6. A liquid-crystalline medium having two or more liquid-crystalline components, wherein said medium comprises at least one compound according to claim 1.

7. In an optical display element containing a liquid-crystalline medium, the improvement wherein said medium is a liquid-crystalline medium according to claim 6.

8. In an electro-optical display element containing a liquid-crystalline medium as a dielectric, the improvement wherein said medium is a liquid-crystalline medium according to claim 6.

* * * * *